(12) United States Patent
Biberger et al.

(10) Patent No.: US 9,216,398 B2
(45) Date of Patent: Dec. 22, 2015

(54) METHOD AND APPARATUS FOR MAKING UNIFORM AND ULTRASMALL NANOPARTICLES

(71) Applicant: SDCmaterials, Inc., Tempe, AZ (US)

(72) Inventors: Maximilian A. Biberger, Scottsdake, AZ (US); Frederick P. Layman, Carefree, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 0 days.

(21) Appl. No.: 14/165,438

(22) Filed: Jan. 27, 2014

(65) Prior Publication Data

US 2014/0209451 A1 Jul. 31, 2014

Related U.S. Application Data

(62) Division of application No. 12/152,096, filed on May 9, 2008, now Pat. No. 8,663,571.

(60) Provisional application No. 60/928,946, filed on May 11, 2007.

(51) Int. Cl.
*B01J 19/08* (2006.01)
*B01J 19/00* (2006.01)
(Continued)

(52) U.S. Cl.
CPC ............... *B01J 19/0013* (2013.01); *B01J 2/16* (2013.01); *B01J 25/00* (2013.01); *B01J 25/02* (2013.01); *B22F 9/12* (2013.01); *F28D 15/00* (2013.01); *F28F 27/00* (2013.01); *B22F 2999/00* (2013.01);
(Continued)

(58) Field of Classification Search
None
See application file for complete search history.

(56) References Cited

U.S. PATENT DOCUMENTS 2,021,936 A 11/1935 Johnstone
2,284,554 A 5/1942 Beyerstedt
(Continued)

FOREIGN PATENT DOCUMENTS

CN 1647858 A 8/2005
CN 101011664 A 8/2007
(Continued)

OTHER PUBLICATIONS

Ahmad, K. et al. (2008). "Hybrid Nanocomposites: A New Route Towards Tougher Alumina Ceramics," *Composites Science and Technology* 68: 1321-1327.
(Continued)

*Primary Examiner* — Kishor Mayekar
(74) *Attorney, Agent, or Firm* — Morrison & Foerster LLP

(57) ABSTRACT

A system comprising: a plasma production chamber configured to produce a plasma; a reaction chamber vaporize a precursor material with the plasma to form a reactive mixture; a quench chamber having a frusto-conical surface and a quench region formed within the quench chamber between an ejection port of the reaction chamber and a cooled mixture outlet, wherein the quench region configured to receive the reactive mixture from the ejection port, to cool the reactive mixture to form a cooled mixture, and to supply the cooled mixture to the cooled mixture outlet; and a conditioning fluid injection ring disposed at the ejection port and configured to flow a conditioning fluid directly into the reactive mixture as the reactive mixture flows through the ejection port, thereby disturbing the flow of the reactive mixture, creating turbulence within the quench region and cooling the reactive mixture to form a cooled mixture comprising condensed nanoparticles.

22 Claims, 3 Drawing Sheets

(51) Int. Cl.

| | | |
|---|---|---|
| *B22F 9/12* | (2006.01) | |
| *F28D 15/00* | (2006.01) | |
| *F28F 27/00* | (2006.01) | |
| *B01J 25/00* | (2006.01) | |
| *B01J 25/02* | (2006.01) | |
| *B01J 2/16* | (2006.01) | |
| *F28D 7/02* | (2006.01) | |
| *F28D 7/08* | (2006.01) | |

(52) U.S. Cl.
CPC . *F28D 7/024* (2013.01); *F28D 7/08* (2013.01); *Y10S 623/92* (2013.01); *Y10S 623/923* (2013.01); *Y10T 137/0391* (2015.04); *Y10T 137/2076* (2015.04); *Y10T 156/15* (2015.01)

(56) References Cited

U.S. PATENT DOCUMENTS

| | | |
|---|---|---|
| 2,419,042 A | 4/1947 | Todd |
| 2,519,531 A | 8/1950 | Worn |
| 2,562,753 A | 7/1951 | Trost |
| 2,689,780 A | 9/1954 | Rice |
| 3,001,402 A | 9/1961 | Koblin |
| 3,042,511 A | 7/1962 | Reding, Jr. |
| 3,067,025 A | 12/1962 | Chisholm |
| 3,145,287 A | 8/1964 | Siebein et al. |
| 3,178,121 A | 4/1965 | Wallace, Jr. |
| 3,179,782 A | 4/1965 | Matvay |
| 3,181,947 A | 5/1965 | Vordahl |
| 3,235,700 A | 2/1966 | Mondain-Monval et al. |
| 3,313,908 A | 4/1967 | Unger et al. |
| 3,387,110 A | 6/1968 | Wendler et al. |
| 3,401,465 A | 9/1968 | Larwill |
| 3,450,926 A | 6/1969 | Kiernan |
| 3,457,788 A | 7/1969 | Miyajima |
| 3,520,656 A | 7/1970 | Yates et al. |
| 3,537,513 A | 11/1970 | Austin |
| 3,552,653 A | 1/1971 | Inoue |
| 3,617,358 A | 11/1971 | Dittrich |
| 3,667,111 A | 6/1972 | Chartet |
| 3,730,827 A | 5/1973 | Matchen et al. |
| 3,741,001 A | 6/1973 | Fletcher et al. |
| 3,752,172 A | 8/1973 | Cohen et al. |
| 3,761,360 A | 9/1973 | Auvil et al. |
| 3,774,442 A | 11/1973 | Gustaysson |
| 3,804,034 A | 4/1974 | Stiglich, Jr. |
| 3,830,756 A | 8/1974 | Sanchez et al. |
| 3,857,744 A | 12/1974 | Moss |
| 3,871,448 A | 3/1975 | Vann et al. |
| 3,892,882 A | 7/1975 | Guest et al. |
| 3,914,573 A | 10/1975 | Muehlberger |
| 3,959,094 A | 5/1976 | Steinberg |
| 3,959,420 A | 5/1976 | Geddes et al. |
| 3,969,482 A | 7/1976 | Teller |
| 4,008,620 A | 2/1977 | Narato et al. |
| 4,018,388 A | 4/1977 | Andrews |
| 4,021,021 A | 5/1977 | Hall et al. |
| 4,127,760 A | 11/1978 | Meyer et al. |
| 4,139,497 A | 2/1979 | Castor et al. |
| 4,146,654 A | 3/1979 | Guyonnet |
| 4,157,316 A | 6/1979 | Thompson et al. |
| 4,171,288 A | 10/1979 | Keith et al. |
| 4,174,298 A | 11/1979 | Antos |
| 4,189,925 A | 2/1980 | Long |
| 4,227,928 A | 10/1980 | Wang |
| 4,248,387 A | 2/1981 | Andrews |
| 4,253,917 A | 3/1981 | Wang |
| 4,260,649 A | 4/1981 | Dension et al. |
| 4,284,609 A | 8/1981 | deVries |
| 4,315,874 A | 2/1982 | Ushida et al. |
| 4,326,492 A | 4/1982 | Leibrand, Sr. et al. |
| 4,344,779 A | 8/1982 | Isserlis |
| 4,369,167 A | 1/1983 | Weir |
| 4,388,274 A | 6/1983 | Rourke et al. |
| 4,419,331 A | 12/1983 | Montalvo |
| 4,431,750 A | 2/1984 | McGinnis et al. |
| 4,436,075 A | 3/1984 | Campbell et al. |
| 4,440,733 A | 4/1984 | Lawson et al. |
| 4,458,138 A | 7/1984 | Adrian et al. |
| 4,459,327 A | 7/1984 | Wang |
| 4,505,945 A | 3/1985 | Dubust et al. |
| 4,506,136 A | 3/1985 | Smyth et al. |
| 4,513,149 A | 4/1985 | Gray et al. |
| 4,523,981 A | 6/1985 | Ang et al. |
| 4,545,872 A | 10/1985 | Sammells et al. |
| RE32,244 E | 9/1986 | Andersen |
| 4,609,441 A | 9/1986 | Frese, Jr. et al. |
| 4,610,857 A | 9/1986 | Ogawa et al. |
| 4,616,779 A | 10/1986 | Serrano et al. |
| 4,723,589 A | 2/1988 | Iyer et al. |
| 4,731,517 A | 3/1988 | Cheney |
| 4,751,021 A | 6/1988 | Mollon et al. |
| 4,764,283 A | 8/1988 | Ashbrook et al. |
| 4,765,805 A | 8/1988 | Wahl et al. |
| 4,780,591 A | 10/1988 | Bernecki et al. |
| 4,824,624 A | 4/1989 | Palicka et al. |
| 4,836,084 A | 6/1989 | Vogelesang et al. |
| 4,855,505 A | 8/1989 | Koll |
| 4,866,240 A | 9/1989 | Webber |
| 4,877,937 A | 10/1989 | Müller |
| 4,885,038 A | 12/1989 | Anderson et al. |
| 4,921,586 A | 5/1990 | Molter |
| 4,970,364 A | 11/1990 | Müller |
| 4,982,050 A | 1/1991 | Gammie et al. |
| 4,983,555 A | 1/1991 | Roy et al. |
| 4,987,033 A | 1/1991 | Abkowitz et al. |
| 5,006,163 A | 4/1991 | Benn et al. |
| 5,015,863 A | 5/1991 | Takeshima et al. |
| 5,041,713 A | 8/1991 | Weidman |
| 5,043,548 A | 8/1991 | Whitney et al. |
| 5,070,064 A | 12/1991 | Hsu et al. |
| 5,073,193 A | 12/1991 | Chaklader et al. |
| 5,133,190 A | 7/1992 | Abdelmalek |
| 5,151,296 A | 9/1992 | Tokunaga |
| 5,157,007 A | 10/1992 | Domesle et al. |
| 5,187,140 A | 2/1993 | Thorsteinson et al. |
| 5,192,130 A | 3/1993 | Endo et al. |
| 5,217,746 A | 6/1993 | Lenling et al. |
| 5,225,656 A | 7/1993 | Frind |
| 5,230,844 A | 7/1993 | Macaire et al. |
| 5,233,153 A | 8/1993 | Coats |
| 5,269,848 A | 12/1993 | Nakagawa |
| 5,294,242 A | 3/1994 | Zurecki et al. |
| 5,330,945 A | 7/1994 | Beckmeyer et al. |
| 5,338,716 A | 8/1994 | Triplett et al. |
| 5,357,075 A | 10/1994 | Muehlberger |
| 5,369,241 A | 11/1994 | Taylor et al. |
| 5,371,049 A | 12/1994 | Moffett et al. |
| 5,372,629 A | 12/1994 | Anderson et al. |
| 5,392,797 A | 2/1995 | Welch |
| 5,436,080 A | 7/1995 | Inoue et al. |
| 5,439,865 A | 8/1995 | Abe et al. |
| 5,442,153 A | 8/1995 | Marantz et al. |
| 5,452,854 A | 9/1995 | Keller |
| 5,460,701 A | 10/1995 | Parker et al. |
| 5,464,458 A | 11/1995 | Yamamoto |
| 5,485,941 A | 1/1996 | Guyomard et al. |
| 5,486,675 A | 1/1996 | Taylor et al. |
| 5,489,449 A | 2/1996 | Umeya et al. |
| 5,534,149 A | 7/1996 | Birkenbeil et al. |
| 5,534,270 A | 7/1996 | De Castro |
| 5,543,173 A | 8/1996 | Horn, Jr. et al. |
| 5,553,507 A | 9/1996 | Basch et al. |
| 5,558,771 A | 9/1996 | Hagen et al. |
| 5,562,966 A | 10/1996 | Clarke et al. |
| 5,582,807 A | 12/1996 | Liao et al. |
| 5,596,973 A | 1/1997 | Grice |
| 5,611,896 A | 3/1997 | Swanepoel et al. |
| 5,630,322 A | 5/1997 | Heilmann et al. |
| 5,652,304 A | 7/1997 | Calderon et al. |
| 5,714,644 A | 2/1998 | Irgang et al. |
| 5,723,027 A | 3/1998 | Serole |
| 5,723,187 A | 3/1998 | Popoola et al. |
| 5,726,414 A | 3/1998 | Kitahashi et al. |

(56) References Cited

U.S. PATENT DOCUMENTS

| | | |
|---|---|---|
| 5,733,662 A | 3/1998 | Bogachek |
| 5,749,938 A | 5/1998 | Coombs |
| 5,776,359 A | 7/1998 | Schultz et al. |
| 5,788,738 A | 8/1998 | Pirzada et al. |
| 5,804,155 A | 9/1998 | Farrauto et al. |
| 5,811,187 A | 9/1998 | Anderson et al. |
| 5,837,959 A | 11/1998 | Muehlberger et al. |
| 5,851,507 A | 12/1998 | Pirzada et al. |
| 5,853,815 A | 12/1998 | Muehlberger |
| 5,858,470 A | 1/1999 | Bernecki et al. |
| 5,884,473 A | 3/1999 | Noda et al. |
| 5,905,000 A | 5/1999 | Yadav et al. |
| 5,928,806 A | 7/1999 | Olah et al. |
| 5,935,293 A | 8/1999 | Detering et al. |
| 5,973,289 A | 10/1999 | Read et al. |
| 5,989,648 A | 11/1999 | Phillips |
| 5,993,967 A | 11/1999 | Brotzman, Jr. et al. |
| 5,993,988 A | 11/1999 | Ohara et al. |
| 6,004,620 A | 12/1999 | Camm |
| 6,012,647 A | 1/2000 | Ruta et al. |
| 6,033,781 A | 3/2000 | Brotzman, Jr. et al. |
| 6,045,765 A | 4/2000 | Nakatsuji et al. |
| 6,059,853 A | 5/2000 | Coombs |
| 6,066,587 A | 5/2000 | Kurokawa et al. |
| 6,084,197 A | 7/2000 | Fusaro, Jr. |
| 6,093,306 A | 7/2000 | Hanrahan et al. |
| 6,093,378 A | 7/2000 | Deeba et al. |
| 6,102,106 A | 8/2000 | Manning et al. |
| 6,117,376 A | 9/2000 | Merkel |
| 6,140,539 A | 10/2000 | Sander et al. |
| 6,168,694 B1 | 1/2001 | Huang et al. |
| 6,190,627 B1 | 2/2001 | Hoke et al. |
| 6,213,049 B1 | 4/2001 | Yang |
| 6,214,195 B1 | 4/2001 | Yadav et al. |
| 6,228,904 B1 | 5/2001 | Yadav et al. |
| 6,231,792 B1 | 5/2001 | Overbeek et al. |
| 6,254,940 B1 | 7/2001 | Pratsinis et al. |
| 6,261,484 B1 | 7/2001 | Phillips et al. |
| 6,267,864 B1 | 7/2001 | Yadav et al. |
| 6,322,756 B1 | 11/2001 | Arno et al. |
| 6,342,465 B1 | 1/2002 | Klein et al. |
| 6,344,271 B1 | 2/2002 | Yadav et al. |
| 6,362,449 B1 | 3/2002 | Hadidi et al. |
| 6,379,419 B1 | 4/2002 | Celik et al. |
| 6,387,560 B1 | 5/2002 | Yadav et al. |
| 6,395,214 B1 | 5/2002 | Kear et al. |
| 6,398,843 B1 | 6/2002 | Tarrant |
| 6,399,030 B1 | 6/2002 | Nolan |
| 6,409,851 B1 | 6/2002 | Sethuram et al. |
| 6,413,781 B1 | 7/2002 | Geis et al. |
| 6,413,898 B1 | 7/2002 | Faber et al. |
| 6,416,818 B1 | 7/2002 | Aikens et al. |
| RE37,853 E | 9/2002 | Detering et al. |
| 6,444,009 B1 | 9/2002 | Liu et al. |
| 6,475,951 B1 | 11/2002 | Domesle et al. |
| 6,488,904 B1 | 12/2002 | Cox et al. |
| 6,491,423 B1 | 12/2002 | Skibo et al. |
| 6,506,995 B1 | 1/2003 | Fusaro, Jr. et al. |
| 6,517,800 B1 | 2/2003 | Cheng et al. |
| 6,524,662 B2 | 2/2003 | Jang et al. |
| 6,531,704 B2 | 3/2003 | Yadav et al. |
| 6,548,445 B1 | 4/2003 | Buysch et al. |
| 6,554,609 B2 | 4/2003 | Yadav et al. |
| 6,562,304 B1 | 5/2003 | Mizrahi |
| 6,562,495 B2 | 5/2003 | Yadav et al. |
| 6,569,393 B1 | 5/2003 | Hoke et al. |
| 6,569,397 B1 | 5/2003 | Yadav et al. |
| 6,569,518 B2 | 5/2003 | Yadav et al. |
| 6,572,672 B2 | 6/2003 | Yadav et al. |
| 6,579,446 B1 | 6/2003 | Teran et al. |
| 6,596,187 B2 | 7/2003 | Coll et al. |
| 6,603,038 B1 | 8/2003 | Hagemeyer et al. |
| 6,607,821 B2 | 8/2003 | Yadav et al. |
| 6,610,355 B2 | 8/2003 | Yadav et al. |
| 6,623,559 B2 | 9/2003 | Huang |
| 6,635,357 B2 | 10/2003 | Moxson et al. |
| 6,641,775 B2 | 11/2003 | Vigliotti et al. |
| 6,652,822 B2 | 11/2003 | Phillips et al. |
| 6,652,967 B2 | 11/2003 | Yadav et al. |
| 6,669,823 B1 | 12/2003 | Sarkas et al. |
| 6,682,002 B2 | 1/2004 | Kyotani |
| 6,689,192 B1 | 2/2004 | Phillips et al. |
| 6,699,398 B1 | 3/2004 | Kim |
| 6,706,097 B2 | 3/2004 | Zornes |
| 6,706,660 B2 | 3/2004 | Park |
| 6,710,207 B2 | 3/2004 | Bogan, Jr. et al. |
| 6,713,176 B2 | 3/2004 | Yadav et al. |
| 6,716,525 B1 | 4/2004 | Yadav et al. |
| 6,744,006 B2 | 6/2004 | Johnson et al. |
| 6,746,791 B2 | 6/2004 | Yadav et al. |
| 6,772,584 B2 | 8/2004 | Chun et al. |
| 6,786,950 B2 | 9/2004 | Yadav et al. |
| 6,813,931 B2 | 11/2004 | Yadav et al. |
| 6,817,388 B2 | 11/2004 | Tsangaris et al. |
| 6,832,735 B2 | 12/2004 | Yadav et al. |
| 6,838,072 B1 | 1/2005 | Kong et al. |
| 6,841,509 B1 | 1/2005 | Hwang et al. |
| 6,855,410 B2 | 2/2005 | Buckley |
| 6,855,426 B2 | 2/2005 | Yadav |
| 6,855,749 B1 | 2/2005 | Yadav et al. |
| 6,858,170 B2 | 2/2005 | Van Thillo et al. |
| 6,886,545 B1 | 5/2005 | Holm |
| 6,891,319 B2 | 5/2005 | Dean et al. |
| 6,896,958 B1 | 5/2005 | Cayton et al. |
| 6,902,699 B2 | 6/2005 | Fritzemeier et al. |
| 6,916,872 B2 | 7/2005 | Yadav et al. |
| 6,919,065 B2 | 7/2005 | Zhou et al. |
| 6,919,527 B2 | 7/2005 | Boulos et al. |
| 6,933,331 B2 | 8/2005 | Yadav et al. |
| 6,972,115 B1 | 12/2005 | Ballard |
| 6,986,877 B2 | 1/2006 | Takikawa et al. |
| 6,994,837 B2 | 2/2006 | Boulos et al. |
| 7,007,872 B2 | 3/2006 | Yadav et al. |
| 7,022,305 B2 | 4/2006 | Drumm et al. |
| 7,052,777 B2 | 5/2006 | Brotzman, Jr. et al. |
| 7,073,559 B2 | 7/2006 | O'Larey et al. |
| 7,074,364 B2 | 7/2006 | Jähn et al. |
| 7,081,267 B2 | 7/2006 | Yadav |
| 7,101,819 B2 | 9/2006 | Rosenflanz et al. |
| 7,147,544 B2 | 12/2006 | Rosenflanz |
| 7,147,894 B2 | 12/2006 | Zhou et al. |
| 7,166,198 B2 | 1/2007 | Van Der Walt et al. |
| 7,166,663 B2 | 1/2007 | Cayton et al. |
| 7,172,649 B2 | 2/2007 | Conrad et al. |
| 7,172,790 B2 | 2/2007 | Koulik et al. |
| 7,178,747 B2 | 2/2007 | Yadav et al. |
| 7,208,126 B2 | 4/2007 | Musick et al. |
| 7,211,236 B2 | 5/2007 | Stark et a |
| 7,217,407 B2 | 5/2007 | Zhang |
| 7,220,398 B2 | 5/2007 | Sutorik et al. |
| 7,255,498 B2 | 8/2007 | Bush et al. |
| 7,265,076 B2 | 9/2007 | Taguchi et al. |
| 7,282,167 B2 | 10/2007 | Carpenter |
| 7,307,195 B2 | 12/2007 | Polverejan et al. |
| 7,323,655 B2 | 1/2008 | Kim |
| 7,384,447 B2 | 6/2008 | Kodas et al. |
| 7,402,899 B1 | 7/2008 | Whiting et al. |
| 7,417,008 B2 | 8/2008 | Richards et al. |
| 7,494,527 B2 | 2/2009 | Jurewicz et al. |
| 7,507,495 B2 | 3/2009 | Wang et al. |
| 7,517,826 B2 | 4/2009 | Fujdala et al. |
| 7,534,738 B2 | 5/2009 | Fujdala et al. |
| 7,541,012 B2 | 6/2009 | Yeung et al. |
| 7,541,310 B2 | 6/2009 | Espinoza et al. |
| 7,557,324 B2 | 7/2009 | Nylen et al. |
| 7,572,315 B2 | 8/2009 | Boulos et al. |
| 7,576,029 B2 | 8/2009 | Saito et al. |
| 7,576,031 B2 | 8/2009 | Beutel et al. |
| 7,601,294 B2 | 10/2009 | Ripley et al. |
| 7,604,843 B1 | 10/2009 | Robinson et al. |
| 7,611,686 B2 | 11/2009 | Alekseeva et al. |
| 7,615,097 B2 | 11/2009 | McKechnie et al. |
| 7,618,919 B2 | 11/2009 | Shimazu et al. |
| 7,622,693 B2 | 11/2009 | Foret |

(56) References Cited

U.S. PATENT DOCUMENTS

| | | |
|---|---|---|
| 7,632,775 B2 | 12/2009 | Zhou et al. |
| 7,635,218 B1 | 12/2009 | Lott |
| 7,674,744 B2 | 3/2010 | Shiratori et al. |
| 7,678,419 B2 | 3/2010 | Kevvitch et al. |
| 7,704,369 B2 | 4/2010 | Olah et al. |
| 7,709,411 B2 | 5/2010 | Zhou et al. |
| 7,709,414 B2 | 5/2010 | Fujdala et al. |
| 7,745,367 B2 | 6/2010 | Fujdala et al. |
| 7,750,265 B2 | 7/2010 | Belashchenko et al. |
| 7,759,279 B2 | 7/2010 | Shiratori et al. |
| 7,759,281 B2 | 7/2010 | Kezuka et al. |
| 7,803,210 B2 | 9/2010 | Sekine et al. |
| 7,842,515 B2 | 11/2010 | Zou et al. |
| 7,851,405 B2 | 12/2010 | Wakamatsu et al. |
| 7,874,239 B2 | 1/2011 | Howland |
| 7,875,573 B2 | 1/2011 | Beutel et al. |
| 7,897,127 B2 | 3/2011 | Layman et al. |
| 7,902,104 B2 | 3/2011 | Kalck et al. |
| 7,905,942 B1 | 3/2011 | Layman |
| 7,935,655 B2 | 5/2011 | Tolmachev |
| 7,951,428 B2 | 5/2011 | Hoerr et al. |
| 8,003,020 B2 | 8/2011 | Jankowiak et al. |
| 8,051,724 B1 | 11/2011 | Layman et al. |
| 8,076,258 B1 | 12/2011 | Biberger |
| 8,080,494 B2 | 12/2011 | Yasuda et al. |
| 8,089,495 B2 | 1/2012 | Keller |
| 8,129,654 B2 | 3/2012 | Lee et al. |
| 8,142,619 B2 | 3/2012 | Layman et al. |
| 8,168,561 B2 | 5/2012 | Virkar |
| 8,173,572 B2 | 5/2012 | Feaviour |
| 8,211,392 B2 | 7/2012 | Grubert et al. |
| 8,258,070 B2 | 9/2012 | Fujdala et al. |
| 8,278,240 B2 | 10/2012 | Tange et al. |
| 8,294,060 B2 | 10/2012 | Mohanty et al. |
| 8,309,489 B2 | 11/2012 | Roldan Cuenya et al. |
| 8,349,761 B2 | 1/2013 | Xia et al. |
| 8,404,611 B2 | 3/2013 | Nakamura et al. |
| 8,470,112 B1 | 6/2013 | Biberger |
| 8,481,449 B1 | 7/2013 | Biberger et al. |
| 8,507,401 B1 | 8/2013 | Biberger et al. |
| 8,507,402 B1 | 8/2013 | Biberger et al. |
| 8,524,631 B2 | 9/2013 | Biberger |
| 8,545,652 B1 | 10/2013 | Biberger |
| 8,557,727 B2 | 10/2013 | Yin et al. |
| 8,574,408 B2 | 11/2013 | Layman |
| 8,574,520 B2 | 11/2013 | Koplin et al. |
| 8,575,059 B1 | 11/2013 | Biberger et al. |
| 8,604,398 B1 | 12/2013 | Layman |
| 8,652,992 B2 | 2/2014 | Yin et al. |
| 8,668,803 B1 | 3/2014 | Biberger |
| 8,669,202 B2 | 3/2014 | van den Hoek et al. |
| 8,679,433 B2 | 3/2014 | Yin et al. |
| 8,821,786 B1 | 9/2014 | Biberger |
| 8,828,328 B1 | 9/2014 | Leamon et al. |
| 8,859,035 B1 | 10/2014 | Leamon |
| 8,877,357 B1 | 11/2014 | Biberger |
| 8,893,651 B1 | 11/2014 | Biberger et al. |
| 8,906,498 B1 | 12/2014 | Biberger |
| 8,932,514 B1 | 1/2015 | Yin et al. |
| 8,992,820 B1 | 3/2015 | Yin et al. |
| 9,023,754 B2 | 5/2015 | Biberger |
| 9,039,916 B1 | 5/2015 | Lehman, Jr. |
| 2001/0004009 A1 | 6/2001 | MacKelvie |
| 2001/0042802 A1 | 11/2001 | Youds |
| 2001/0055554 A1 | 12/2001 | Hoke et al. |
| 2002/0018815 A1 | 2/2002 | Sievers et al. |
| 2002/0068026 A1 | 6/2002 | Murrell et al. |
| 2002/0071800 A1 | 6/2002 | Hoke et al. |
| 2002/0079620 A1 | 6/2002 | DuBuis et al. |
| 2002/0100751 A1 | 8/2002 | Carr |
| 2002/0102674 A1 | 8/2002 | Anderson |
| 2002/0131914 A1 | 9/2002 | Sung |
| 2002/0143417 A1 | 10/2002 | Ito et al. |
| 2002/0168466 A1 | 11/2002 | Tapphorn et al. |
| 2002/0182735 A1 | 12/2002 | Kibby et al. |
| 2002/0183191 A1 | 12/2002 | Faber et al. |
| 2002/0192129 A1 | 12/2002 | Shamouilian et al. |
| 2003/0036786 A1 | 2/2003 | Duren et al. |
| 2003/0042232 A1 | 3/2003 | Shimazu |
| 2003/0047617 A1 | 3/2003 | Shanmugham et al. |
| 2003/0066800 A1 | 4/2003 | Saim et al. |
| 2003/0085663 A1 | 5/2003 | Horsky |
| 2003/0102099 A1 | 6/2003 | Yadav et al. |
| 2003/0108459 A1 | 6/2003 | Wu et al. |
| 2003/0110931 A1 | 6/2003 | Aghajanian et al. |
| 2003/0129098 A1 | 7/2003 | Endo et al. |
| 2003/0139288 A1 | 7/2003 | Cai et al. |
| 2003/0143153 A1 | 7/2003 | Boulos et al. |
| 2003/0172772 A1 | 9/2003 | Sethuram et al. |
| 2003/0223546 A1 | 12/2003 | McGregor et al. |
| 2004/0009118 A1 | 1/2004 | Phillips et al. |
| 2004/0023302 A1 | 2/2004 | Archibald et al. |
| 2004/0023453 A1 | 2/2004 | Xu et al. |
| 2004/0065170 A1 | 4/2004 | Wu et al. |
| 2004/0077494 A1 | 4/2004 | LaBarge et al. |
| 2004/0103751 A1 | 6/2004 | Joseph et al. |
| 2004/0109523 A1 | 6/2004 | Singh et al. |
| 2004/0119064 A1 | 6/2004 | Narayan et al. |
| 2004/0127586 A1 | 7/2004 | Jin et al. |
| 2004/0129222 A1 | 7/2004 | Nylen et al. |
| 2004/0166036 A1 | 8/2004 | Chen et al. |
| 2004/0167009 A1 | 8/2004 | Kuntz et al. |
| 2004/0176246 A1 | 9/2004 | Shirk et al. |
| 2004/0208805 A1 | 10/2004 | Fincke et al. |
| 2004/0213998 A1 | 10/2004 | Hearley et al. |
| 2004/0235657 A1 | 11/2004 | Xiao et al. |
| 2004/0238345 A1 | 12/2004 | Koulik et al. |
| 2004/0251017 A1 | 12/2004 | Pillion et al. |
| 2004/0251241 A1 | 12/2004 | Blutke et al. |
| 2005/0000321 A1 | 1/2005 | O'Larey et al. |
| 2005/0000950 A1 | 1/2005 | Schroder et al. |
| 2005/0058797 A1 | 3/2005 | Sen et al. |
| 2005/0066805 A1 | 3/2005 | Park et al. |
| 2005/0070431 A1 | 3/2005 | Alvin et al. |
| 2005/0077034 A1 | 4/2005 | King |
| 2005/0097988 A1 | 5/2005 | Kodas et al. |
| 2005/0106865 A1 | 5/2005 | Chung et al. |
| 2005/0133121 A1 | 6/2005 | Subramanian et al. |
| 2005/0153069 A1 | 7/2005 | Tapphorn et al. |
| 2005/0163673 A1 | 7/2005 | Johnson et al. |
| 2005/0199739 A1 | 9/2005 | Kuroda et al. |
| 2005/0211018 A1 | 9/2005 | Jurewicz et al. |
| 2005/0220695 A1 | 10/2005 | Abatzoglou et al. |
| 2005/0227864 A1 | 10/2005 | Sutorik et al. |
| 2005/0233380 A1 | 10/2005 | Pesiri et al. |
| 2005/0240069 A1 | 10/2005 | Polverejan et al. |
| 2005/0258766 A1 | 11/2005 | Kim |
| 2005/0274646 A1 | 12/2005 | Lawson et al. |
| 2005/0275143 A1 | 12/2005 | Toth |
| 2006/0043651 A1 | 3/2006 | Yamamoto et al. |
| 2006/0051505 A1 | 3/2006 | Kortshagen et al. |
| 2006/0068989 A1 | 3/2006 | Ninomiya et al. |
| 2006/0094595 A1 | 5/2006 | Labarge |
| 2006/0096393 A1 | 5/2006 | Pesiri |
| 2006/0105910 A1 | 5/2006 | Zhou et al. |
| 2006/0108332 A1 | 5/2006 | Belashchenko |
| 2006/0153728 A1 | 7/2006 | Schoenung et al. |
| 2006/0153765 A1 | 7/2006 | Pham-Huu et al. |
| 2006/0159596 A1 | 7/2006 | De La Veaux et al. |
| 2006/0166809 A1 | 7/2006 | Malek et al. |
| 2006/0211569 A1 | 9/2006 | Dang et al. |
| 2006/0213326 A1 | 9/2006 | Gollob et al. |
| 2006/0222780 A1 | 10/2006 | Gurevich et al. |
| 2006/0231525 A1 | 10/2006 | Asakawa et al. |
| 2007/0020167 A1 | 1/2007 | Han et al. |
| 2007/0044513 A1 | 3/2007 | Kear et al. |
| 2007/0048206 A1 | 3/2007 | Hung et al. |
| 2007/0049484 A1 | 3/2007 | Kear et al. |
| 2007/0063364 A1 | 3/2007 | Hsiao et al. |
| 2007/0084308 A1 | 4/2007 | Nakamura et al. |
| 2007/0084834 A1 | 4/2007 | Hanus et al. |
| 2007/0087934 A1 | 4/2007 | Martens et al. |
| 2007/0092768 A1 | 4/2007 | Lee et al. |
| 2007/0153390 A1 | 7/2007 | Nakamura et al. |

(56) References Cited

U.S. PATENT DOCUMENTS

| | | |
|---|---|---|
| 2007/0161506 A1 | 7/2007 | Saito et al. |
| 2007/0163385 A1 | 7/2007 | Takahashi et al. |
| 2007/0172721 A1 | 7/2007 | Pak et al. |
| 2007/0173403 A1 | 7/2007 | Koike et al. |
| 2007/0178673 A1 | 8/2007 | Gole et al. |
| 2007/0221404 A1 | 9/2007 | Das et al. |
| 2007/0253874 A1 | 11/2007 | Foret |
| 2007/0259768 A1 | 11/2007 | Kear et al. |
| 2007/0266825 A1 | 11/2007 | Ripley et al. |
| 2007/0292321 A1 | 12/2007 | Plischke et al. |
| 2008/0006954 A1 | 1/2008 | Yubuta et al. |
| 2008/0026041 A1 | 1/2008 | Tepper et al. |
| 2008/0031806 A1 | 2/2008 | Gavenonis et al. |
| 2008/0038578 A1 | 2/2008 | Li |
| 2008/0045405 A1 | 2/2008 | Beutel et al. |
| 2008/0047261 A1 | 2/2008 | Han et al. |
| 2008/0056977 A1* | 3/2008 | Hung et al. .......... 423/291 |
| 2008/0057212 A1 | 3/2008 | Dorier et al. |
| 2008/0064769 A1 | 3/2008 | Sato et al. |
| 2008/0104735 A1 | 5/2008 | Howland |
| 2008/0105083 A1 | 5/2008 | Nakamura et al. |
| 2008/0108005 A1 | 5/2008 | Carpenter |
| 2008/0116178 A1 | 5/2008 | Weidman |
| 2008/0125308 A1 | 5/2008 | Fujdala et al. |
| 2008/0125313 A1 | 5/2008 | Fujdala et al. |
| 2008/0138651 A1 | 6/2008 | Doi et al. |
| 2008/0175936 A1 | 7/2008 | Tokita et al. |
| 2008/0187714 A1 | 8/2008 | Wakamatsu et al. |
| 2008/0202288 A1 | 8/2008 | McKechnie et al. |
| 2008/0206562 A1 | 8/2008 | Stucky et al. |
| 2008/0207858 A1 | 8/2008 | Kowaleski et al. |
| 2008/0248704 A1 | 10/2008 | Mathis et al. |
| 2008/0274344 A1 | 11/2008 | Vieth et al. |
| 2008/0277092 A1 | 11/2008 | Layman et al. |
| 2008/0277264 A1 | 11/2008 | Sprague |
| 2008/0277266 A1 | 11/2008 | Layman |
| 2008/0277268 A1 | 11/2008 | Layman |
| 2008/0277269 A1 | 11/2008 | Layman et al. |
| 2008/0277270 A1 | 11/2008 | Biberger et al. |
| 2008/0277271 A1 | 11/2008 | Layman |
| 2008/0280049 A1 | 11/2008 | Kevwitch et al. |
| 2008/0280751 A1 | 11/2008 | Harutyunyan et al. |
| 2008/0280756 A1 | 11/2008 | Biberger |
| 2008/0283411 A1 | 11/2008 | Eastman et al. |
| 2008/0283498 A1 | 11/2008 | Yamazaki |
| 2008/0307960 A1 | 12/2008 | Hendrickson et al. |
| 2009/0010801 A1 | 1/2009 | Murphy et al. |
| 2009/0018008 A1 | 1/2009 | Jankowiak et al. |
| 2009/0054230 A1 | 2/2009 | Veeraraghavan et al. |
| 2009/0081092 A1 | 3/2009 | Yang et al. |
| 2009/0088585 A1 | 4/2009 | Schammel et al. |
| 2009/0092887 A1 | 4/2009 | McGrath et al. |
| 2009/0098402 A1 | 4/2009 | Kang et al. |
| 2009/0114568 A1 | 5/2009 | Trevino et al. |
| 2009/0162991 A1 | 6/2009 | Beneyton et al. |
| 2009/0168506 A1 | 7/2009 | Han et al. |
| 2009/0170242 A1 | 7/2009 | Lin et al. |
| 2009/0181474 A1 | 7/2009 | Nagai |
| 2009/0200180 A1 | 8/2009 | Capote et al. |
| 2009/0208367 A1 | 8/2009 | Calio et al. |
| 2009/0209408 A1 | 8/2009 | Kitamura et al. |
| 2009/0223410 A1 | 9/2009 | Jun et al. |
| 2009/0253037 A1 | 10/2009 | Park et al. |
| 2009/0274897 A1 | 11/2009 | Kaner et al. |
| 2009/0274903 A1 | 11/2009 | Addiego |
| 2009/0286899 A1 | 11/2009 | Hofmann et al. |
| 2009/0320449 A1 | 12/2009 | Beutel et al. |
| 2009/0324468 A1 | 12/2009 | Golden et al. |
| 2010/0050868 A1 | 3/2010 | Kuznicki et al. |
| 2010/0089002 A1 | 4/2010 | Merkel |
| 2010/0092358 A1 | 4/2010 | Koegel et al. |
| 2010/0124514 A1 | 5/2010 | Chelluri et al. |
| 2010/0166629 A1 | 7/2010 | Deeba |
| 2010/0180581 A1 | 7/2010 | Grubert et al. |
| 2010/0180582 A1 | 7/2010 | Mueller-Stach et al. |
| 2010/0186375 A1 | 7/2010 | Kazi et al. |
| 2010/0240525 A1 | 9/2010 | Golden et al. |
| 2010/0275781 A1 | 11/2010 | Tsangaris |
| 2010/0323118 A1 | 12/2010 | Mohanty et al. |
| 2011/0006463 A1 | 1/2011 | Layman |
| 2011/0030346 A1 | 2/2011 | Neubauer et al. |
| 2011/0049045 A1 | 3/2011 | Hurt et al. |
| 2011/0052467 A1 | 3/2011 | Chase et al. |
| 2011/0143041 A1 | 6/2011 | Layman et al. |
| 2011/0143915 A1 | 6/2011 | Yin et al. |
| 2011/0143916 A1 | 6/2011 | Leamon |
| 2011/0143926 A1 | 6/2011 | Yin et al. |
| 2011/0143930 A1 | 6/2011 | Yin et al. |
| 2011/0143933 A1 | 6/2011 | Yin et al. |
| 2011/0144382 A1 | 6/2011 | Yin et al. |
| 2011/0152550 A1 | 6/2011 | Grey et al. |
| 2011/0158871 A1 | 6/2011 | Arnold et al. |
| 2011/0174604 A1 | 7/2011 | Duesel et al. |
| 2011/0243808 A1 | 10/2011 | Fossey et al. |
| 2011/0245073 A1 | 10/2011 | Oljaca et al. |
| 2011/0247336 A9 | 10/2011 | Farsad et al. |
| 2011/0305612 A1 | 12/2011 | Müller-Stach et al. |
| 2012/0023909 A1 | 2/2012 | Lambert et al. |
| 2012/0045373 A1 | 2/2012 | Biberger |
| 2012/0063963 A1 | 3/2012 | Watanabe et al. |
| 2012/0097033 A1 | 4/2012 | Arnold et al. |
| 2012/0122660 A1 | 5/2012 | Andersen et al. |
| 2012/0124974 A1 | 5/2012 | Li et al. |
| 2012/0171098 A1 | 7/2012 | Hung et al. |
| 2012/0214666 A1 | 8/2012 | van den Hoek et al. |
| 2012/0263633 A1 | 10/2012 | Koplin et al. |
| 2012/0285548 A1 | 11/2012 | Layman et al. |
| 2012/0308467 A1 | 12/2012 | Carpenter et al. |
| 2012/0313269 A1 | 12/2012 | Kear et al. |
| 2013/0034472 A1 | 2/2013 | Cantrell et al. |
| 2013/0064750 A1 | 3/2013 | Zettl |
| 2013/0079216 A1 | 3/2013 | Biberger et al. |
| 2013/0125970 A1 | 5/2013 | Ko et al. |
| 2013/0213018 A1 | 8/2013 | Yin et al. |
| 2013/0270355 A1 | 10/2013 | Cotler et al. |
| 2013/0280528 A1 | 10/2013 | Biberger |
| 2013/0281288 A1 | 10/2013 | Biberger et al. |
| 2013/0294989 A1 | 11/2013 | Koch et al. |
| 2013/0316896 A1 | 11/2013 | Biberger |
| 2013/0331257 A1 | 12/2013 | Barcikowski et al. |
| 2013/0345047 A1 | 12/2013 | Biberger et al. |
| 2014/0018230 A1 | 1/2014 | Yin et al. |
| 2014/0120355 A1 | 5/2014 | Biberger |
| 2014/0128245 A1 | 5/2014 | Yin et al. |
| 2014/0140909 A1 | 5/2014 | Qi et al. |
| 2014/0148331 A1 | 5/2014 | Biberger et al. |
| 2014/0161693 A1 | 6/2014 | Brown et al. |
| 2014/0228201 A1 | 8/2014 | Mendoza Gómez et al. |
| 2014/0243187 A1 | 8/2014 | Yin et al. |
| 2014/0249021 A1 | 9/2014 | Van Den Hoek et al. |
| 2014/0252270 A1 | 9/2014 | Lehman, Jr. |
| 2014/0263190 A1 | 9/2014 | Biberger et al. |
| 2014/0318318 A1 | 10/2014 | Layman et al. |
| 2014/0338519 A1 | 11/2014 | Biberger |
| 2015/0093312 A1 | 4/2015 | Yin et al. |
| 2015/0140317 A1 | 5/2015 | Biberger et al. |
| 2015/0141236 A1 | 5/2015 | Yin et al. |
| 2015/0165418 A1 | 6/2015 | Kearl et al. |
| 2015/0165434 A1 | 6/2015 | Yin et al. |

FOREIGN PATENT DOCUMENTS

| | | |
|---|---|---|
| CN | 101301610 A | 11/2008 |
| DE | 34 45 273 A1 | 6/1986 |
| EP | 0 347 386 A1 | 12/1989 |
| EP | 0 385 742 A1 | 9/1990 |
| EP | 1 134 302 A1 | 9/2001 |
| EP | 1 256 378 A2 | 11/2002 |
| EP | 1 619 168 A1 | 1/2006 |
| EP | 1 721 690 A1 | 11/2006 |
| EP | 1 790 612 A1 | 5/2007 |
| EP | 1 955 765 A1 | 8/2008 |
| GB | 1 307 941 A | 2/1973 |
| JP | 49-31571 A | 3/1974 |

(56) References Cited

FOREIGN PATENT DOCUMENTS

| | | |
|---|---|---|
| JP | 56-146804 A | 11/1981 |
| JP | 58-160794 A | 9/1983 |
| JP | 61-086815 A | 5/1986 |
| JP | 62-102827 A | 5/1987 |
| JP | 63-214342 A | 9/1988 |
| JP | 1-164795 A | 6/1989 |
| JP | 1-275708 A | 11/1989 |
| JP | 2-6339 A | 1/1990 |
| JP | 3-226509 A | 10/1991 |
| JP | 5-193909 A | 8/1993 |
| JP | 05-228361 A | 9/1993 |
| JP | 05-324094 A | 12/1993 |
| JP | 6-93309 A | 4/1994 |
| JP | 6-135797 A | 5/1994 |
| JP | 6-172820 A | 6/1994 |
| JP | 6-272012 A | 9/1994 |
| JP | H6-065772 U | 9/1994 |
| JP | 07-031873 A | 2/1995 |
| JP | 7-120176 A | 5/1995 |
| JP | 7-138020 A | 5/1995 |
| JP | 7-207381 A | 8/1995 |
| JP | 07-256116 A | 10/1995 |
| JP | 8-158033 A | 6/1996 |
| JP | 8-215576 A | 8/1996 |
| JP | 8-217420 A | 8/1996 |
| JP | 9-141087 A | 6/1997 |
| JP | 10-130810 A | 5/1998 |
| JP | 10-249198 A | 9/1998 |
| JP | 11-502760 A | 3/1999 |
| JP | 11-300198 A | 11/1999 |
| JP | 2000-220978 A | 8/2000 |
| JP | 2002-88486 A | 3/2002 |
| JP | 2002-241812 A | 8/2002 |
| JP | 2002-336688 A | 11/2002 |
| JP | 2003-126694 A | 5/2003 |
| JP | 2004-233007 A | 8/2004 |
| JP | 2004-249206 A | 9/2004 |
| JP | 2004-290730 A | 10/2004 |
| JP | 2005-503250 A | 2/2005 |
| JP | 2005-122621 A | 5/2005 |
| JP | 2005-218937 A | 8/2005 |
| JP | 2005-342615 A | 12/2005 |
| JP | 2006-001779 A | 1/2006 |
| JP | 2006-508885 A | 3/2006 |
| JP | 2006-87965 A | 4/2006 |
| JP | 2006-247446 A | 9/2006 |
| JP | 2006-260385 A | 9/2006 |
| JP | 2006-272265 A | 10/2006 |
| JP | 2006-326554 A | 12/2006 |
| JP | 2007-29859 A | 2/2007 |
| JP | 2007-44585 A | 2/2007 |
| JP | 2007-46162 A | 2/2007 |
| JP | 2007-138287 A | 6/2007 |
| JP | 2007-203129 A | 8/2007 |
| SU | 493241 A | 3/1976 |
| TW | 200611449 | 4/2006 |
| TW | 201023207 | 6/2010 |
| WO | WO-96/28577 A1 | 9/1996 |
| WO | WO-00/16882 | 3/2000 |
| WO | WO-00/72965 A1 | 12/2000 |
| WO | WO-02/092503 A1 | 11/2002 |
| WO | WO-03/094195 A1 | 11/2003 |
| WO | WO-2004/052778 A2 | 6/2004 |
| WO | WO-2005/063390 A1 | 7/2005 |
| WO | WO-2006/079213 A1 | 8/2006 |
| WO | WO-2006/096205 A2 | 9/2006 |
| WO | WO-2007/144447 A1 | 12/2007 |
| WO | WO-2008/088649 A1 | 7/2008 |
| WO | WO-2008/092478 A1 | 8/2008 |
| WO | WO-2008/130451 A2 | 10/2008 |
| WO | WO-2008-130451 A3 | 10/2008 |
| WO | WO-2009/017479 A1 | 2/2009 |
| WO | WO-2011/081833 A1 | 7/2011 |
| WO | WO-2012/028695 A2 | 3/2012 |
| WO | WO-2013/028575 A1 | 2/2013 |
| WO | WO-2013/093597 A2 | 6/2013 |
| WO | WO-2013/151557 A1 | 10/2013 |

OTHER PUBLICATIONS

Babin, A. et al. (1985). "Solvents Used in the Arts," *Center for Safety in the Arts*: 16 pages.

Bateman, J. E. et al. (Dec. 17, 1998). "Alkylation of Porous Silicon by Direct Reaction with Alkenes and Alkynes," *Angew. Chem Int. Ed.* 37(19):2683-2685.

Carrot, G. et al. (Sep. 17, 2002). "Surface-Initiated Ring-Opening Polymerization: A Versatile Method for Nanoparticle Ordering," *Macromolecules* 35(22):8400-8404.

Chaim, R. et al. (2009). "Densification of Nanocrystalline $Y_2O_3$ Ceramic Powder by Spark Plasma Sintering," *Journal of European Ceramic Society* 29: 91-98.

Chau, J. K. H. et al. (2005). "Microwave Plasma Synthesis of Silver Nanopowders," *Materials Letters* 59: 905-908.

Chen, H.-S. et al. (Jul. 3, 2001). "On the Photoluminescence of Si Nanoparticles," *Mater. Phys. Mech.* 4:62-66.

Chen, W.-J. et al. (Mar. 18, 2008). "Functional $Fe_3O_4/TiO_2$ Core/Shell Magnetic Nanoparticles as Photokilling Agents for Pathogenic Bacteria," *Small* 4(4): 485-491.

Das, N. et al. (2001). "Influence of the Metal Function in the "One-Pot" Synthesis of 4-Methyl-2-Pentanone (Methyl Isobutyl Ketone) from Acetone Over Palladium Supported on Mg(Al)O Mixed Oxides Catalysts," *Catalysis Letters* 71(3-4): 181-185.

Faber, K. T. et al. (Sep. 1988). "Toughening by Stress-Induced Microcracking in Two-Phase Ceramics," *Journal of the American Ceramic Society* 71: C-399-C401.

Fauchais, P. et al. (Jun. 1989). "La Projection Par Plasma: Une Revue," *Ann. Phys. Fr.* 14(3):261-310.

Fauchais, P. et al. (Jan. 1993). "Les Dépôts Par Plasma Thermique," *Revue Générale De L'Electricité*, RGE, Paris, France, No. 2, pp. 7-12 (in French).

Fauchais, P. et al. (Jan. 1996). "Plasma Spray: Study of the Coating Generation," *Ceramics International* 22(4):295-303.

Fojtik, A. et al. (Apr. 29, 1994). "Luminescent Colloidal Silicon Particles,"*Chemical Physics Letters* 221:363-367.

Fojtik, A. (Jan. 13, 2006). "Surface Chemistry of Luminescent Colloidal Silicon Nanoparticles," *J. Phys. Chem. B*. 110(5):1994-1998.

Gangeri, M. et al. (2009). "Fe and Pt Carbon Nanotubes for the Electrocatalytic Conversion of Carbon Dioxide to Oxygenates," *Catalysis Today* 143: 57-63.

Gutsch, A. et al. (2002). "Gas-Phase Production of Nanoparticles," *Kona* No. 20, pp. 24-37.

Han, B. Q. et al. (Jan. 2004). "Deformation Mechanisms and Ductility of Nanostructured Al Alloys", *Mat. Res. Soc. Symp. Proc.* 821:P9.1.1-P9.1.6.

Heberlein, J. (2002). "New Approaches in Thermal Plasma Technology", *Pure Appl. Chem.* 74(3):327-335.

Hua, F. et al. (Mar. 2006). "Organically Capped Silicon Nanoparticles With Blue Photoluminescence Prepared by Hydrosilylation Followed by Oxidation," *Langmuir* 22(9):4363-4370.

Ihlein, G. et al.(1998). "Ordered Porous Materials as Media for the Organization of Matter on the Nanoscale," *Applied Organometallic Chemistry* 12: 305-314.

Ji, Y. et al. (Nov. 2002) "Processing and Mechanical Properties of $Al_2O_3$-5 vol.% Cr Nanocomposites," *Journal of the European Ceramic Society* 22(12):1927-1936.

Jouet, R. J. et al. (Jan. 25, 2005). "Surface Passivation of Bare Aluminum Nanoparticles Using Perfluoroalkyl Carboxylic Acids," *Chem. Mater*.17(11):2987-2996.

Kenvin, J. C. et al. (1992). "Supported Catalysts Prepared from Mononuclear Copper Complexes: Catalytic Properties", *J. Catalysis* 135:81-91.

Konrad, H. et al. (1996). "Nanostructured Cu-Bi Alloys Prepared by Co-Evaporation in a Continuous Gas Flow," *NanoStructured Materials* 7(6):605-610.

Kim, N. Y. et al. (Mar. 5, 1997). "Thermal Derivatization of Porous Silicon with Alcohols," *J. Am. Chem. Soc.* 1 19(9):2297-2298.

(56) References Cited

OTHER PUBLICATIONS

Kwon, Y.-S. et al. (Apr. 30, 2003). "Passivation Process for Superfine Aluminum Powders Obtained by Electrical Explosion of Wires," *Applied Surface Science* 211:57-67.

Lakis, R. E. et al. (1995). "Alumina-Supported Pt-Rh Catalysts: I. Microstructural Characterization," *Journal of Catalysis* 154: 261-275.

Langner, A. et al. (Aug. 25, 2005). "Controlled Silicon Surface Functionalization by Alkene Hydrosilylation," *J. Am. Chem. Soc.* 127(37):12798-12799.

Li, D. et al. (Apr. 9, 2005). "Environmentally Responsive "Hairy" Nanoparticles: Mixed Homopolymer Brushes on Silica Nanoparticles Synthesized by Living Radical Polymerization Techniques," *J. Am. Chem. Soc.* 127(7):6248-6256.

Li, X. et al. (May 25, 2004). "Surface Functionalization of Silicon Nanoparticles Produced by Laser-Driven Pyrolysis of Silane Followed by HF-$HNO_3$ Etching," *Langmuir* 20(11):4720-4727.

Liao, Y.-C. et al. (Jun. 27, 2006). "Self-Assembly of Organic Monolayers on Aerosolized Silicon Nanoparticles," *J.Am. Chem. Soc.* 128(28):9061-9065.

Liu, S.-M. et al. (Jan. 13, 2006). "Enhanced Photoluminescence from Si Nano-Organosols by Functionalization With Alkenes and Their Size Evolution," *Chem. Mater.* 18(3):637-642.

Luo, J. et al. (2008). "Core/Shell Nanoparticles as Electrocatalysts for Fuel Cell Reactions," *Advanced Materials* 20: 4342-4347.

Mignard, D. et al. (2003). "Methanol Synthesis from Flue-Gas $CO_2$ and Renewable Electricity: A Feasibility Study," *International Journal of Hydrogen Energy* 28: 455-464.

Mühlenweg, H. et al. (2004). "Gas-Phase Reactions—Open Up New Roads to Nanoproducts," *Degussa ScienceNewsletter* No. 08, pp. 12-16.

Nagai, Y. et al. (Jul. 3, 2006). "Sintering Inhibition Mechanism of Platinum Supported on Ceria-Based Oxide and Pt-Oxide-Support Interaction," *J. Catalysis* 242:103-109.

NASA (2009). "Enthalpy," Article located at http://www.grc.nasa.gov/WWW/K-12/airplane/enthalpy.htrnl, published by National Aeronautics and Space Administration on Nov. 23, 2009, 1 page.

Neiner, D. (Aug. 5, 2006). "Low-Temperature Solution Route to Macroscopic Amounts of Hydrogen Terminated Silicon Nanoparticles," *J. Am. Chem. Soc.* 128:11016-11017.

Netzer, L. et al. (1983). "A New Approach to Construction of Artificial Monolayer Assemblies," *J. Am. Chem. Soc.* 105(3):674-676.

Park, H.-Y. et al. (May 30, 2007). "Fabrication of Magnetic Core@Shell Fe Oxide@Au Nanoparticles for Interfacial Bioactivity and Bio-Separation," *Langmuir* 23: 9050-9056.

Park, N.-G. et al. (Feb. 17, 2004). "Morphological and Photoelectrochemical Characterization of Core-Shell Nanoparticle Films for Dye-Sensitized Solar Cells: Zn-O Type Shell on $SnO_2$ and $TiO_2$ Cores," *Langmuir* 20: 4246-4253.

"Plasma Spray and Wire Flame Spray Product Group," located at http://www.processmaterials.com/spray.html, published by Process Materials, Inc., last accessed Aug. 5, 2013, 2 pages.

"Platinum Group Metals: Annual Review 1996" (Oct. 1997). Engineering and Mining Journal, p. 63.

Rahaman, R. A. et al. (1995). "Synthesis of Powders," in *Ceramic Processing and Sintering*. Marcel Decker, Inc., New York, pp. 71-77.

Sailor, M. J. (1997). "Surface Chemistry of Luminescent Silicon Nanocrystallites," *Adv. Mater.* 9(10):783-793.

Schimpf, S. et al. (2002). "Supported Gold Nanoparticles: In-Depth Catalyst Characterization and Application in Hydrogenation and Oxidation Reactions," *Catalysis Today* 2592: 1-16.

Stiles, A. B. (Jan. 1, 1987). "Manufacture of Carbon-Supported Metal Catalysts," in *Catalyst Supports and Supported Catalysts*, Butterworth Publishers, MA, pp. 125-132.

Subramanian, S. et al. (1991). "Structure and Activity of Composite Oxide Supported Platinum-Iridium Catalysts," *Applied Catalysts* 74: 65-81.

Tao, Y.-T. (May 1993). "Structural Comparison of Self-Assembled Monolayers of n-Alkanoic Acids on the surfaces of Silver, Copper, and Aluminum," *J. Am. Chem. Soc.* 115(10):4350-4358.

Ünal, N. et al. (Nov. 2011). "Influence of WC Particles on the Microstructural and Mechanical Properties of 3 mol% $Y_2O_3$ Stabilized $ZrO_2$ Matrix Composites Produced by Hot Pressing," *Journal of the European Ceramic Society* (31)13: 2267-2275.

Vardelle, A. et al. (1996). "Coating Generation: Vaporization of Particles in Plasma Spraying and Splat Formation," Universite de Limoges, 123 Avenue A. Thomas 87000, Limoges, France, *Pure & Appl. Chem.* 68(5):1093-1099.

Vardelle, M. et al. (Jun. 1991). "Experimental Investigation of Powder Vaporization in Thermal Plasma Jets," *Plasma Chemistry and Plasma Processing* 11(2):185-201.

Viswanathan, V. et al. (2006). "Challenges and Advances in Nanocomposite Processing Techniques," *Materials Science and Engineering* R 54: 121-285.

Wan, J. et al. (2005). "Spark Plasma Sintering of Silicon Nitride/Silicon Carbide Nanocomposites with Reduced Additive Amounts," *Scripta Materialia* 53: 663-667.

Yoshida, T. (1994). "The Future of Thermal Plasma Processing for Coating", *Pure & Appl. Chem.* 66(6):1223-1230.

Zou, J. et al. (Jun. 4, 2004). "Solution Synthesis of Ultrastable Luminescent Siloxane-Coated Silicon Nanoparticles," *Nano Letters* 4(7):1181-1186.

Non Final Office Action mailed on May 10, 2011, for U.S. Appl. No. 12/151,935, filed May 8, 2008, 14 pages.

Final Office Action mailed on Nov. 1, 2011, for U.S. Appl. No. 12/151,935, filed May 8, 2008, 10 pages.

Non Final Office Action mailed on Feb. 19, 2010, for U.S. Appl. No. 12/152,109, filed May 9, 2008, Biberger et al., 17 pages.

International Search Report mailed on Aug. 8, 2008, for PCT Patent Application No. PCT/US2008/06003, filed on May 8, 2008, published on Nov. 20, 2008, as WO 2008/140786, 1 page.

Written Opinion mailed on Aug. 8, 2008, for PCT Patent Application No. PCT/US2008/06003, filed on May 8, 2008, published on Nov. 20, 2008, as WO 2008/140786, 8 page.

U.S. Appl. No. 13/291,983, filed Nov. 8, 2011, for Layman et al.
U.S. Appl. No. 12/152,084, filed May 9, 2008, for Biberger.
U.S. Appl. No. 13/028,693, filed Feb. 16, 2011, for Biberger.
U.S. Appl. No. 12/943,909, filed Nov. 10, 2010, for Layman.
U.S. Appl. No. 12/152,111, filed May 9, 2008, for Biberger et al.
U.S. Appl. No. 12/151,830, filed May 8, 2008, for Biberger et al.
U.S. Appl. No. 12/968,248, filed Dec. 14, 2010, for Biberger.
U.S. Appl. No. 12/968,245, filed Dec. 14, 2010, for Biberger.
U.S. Appl. No. 12/968,241, filed Dec. 14, 2010, for Biberger.
U.S. Appl. No. 12/968,239, filed Dec. 14, 2010, for Biberger.
U.S. Appl. No. 12/969,128, filed Dec. 15, 2010, for Biberger.
U.S. Appl. No. 12/962,463, filed Dec. 7, 2010, for Leamon.
U.S. Appl. No. 12/961,030, filed Dec. 6, 2010, for Lehman.
U.S. Appl. No. 12/961,108, filed Dec. 6, 2010, for Lehman.
U.S. Appl. No. 12/961,200, filed Dec. 6, 2010, for Lehman.
U.S. Appl. No. 12/968,253, filed Dec. 14, 2010, for Biberger.
U.S. Appl. No. 12/968,235, filed Dec. 14, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/969,087, filed Dec. 15, 2010, for Biberger.
U.S. Appl. No. 12/962,533, filed Dec. 7, 2010, for Yin et al.
U.S. Appl. No. 12/962,523, filed Dec. 7, 2010, for Yin et al.
U.S. Appl. No. 12/001,643, filed Dec. 11, 2007, for Biberger et al.
U.S. Appl. No. 12/474,081, filed May 28, 2009, for Biberger et al.
U.S. Appl. No. 12/001,602, filed Dec. 11, 2007, for Biberger et al.
U.S. Appl. No. 12/001,644, filed Dec. 11, 2007, for Biberger et al.
U.S. Appl. No. 12/969,457, filed Nov. 15, 2010, for Leamon et al.
U.S. Appl. No. 12/969,503, filed Nov. 15, 2010, for Leamon et al.
U.S. Appl. No. 12/954,813, filed Nov. 26, 2010, for Biberger.
U.S. Appl. No. 12/954,822, filed Nov. 26, 2010, for Biberger.

Birlik, I. et al. (Jun. 15, 2010). "Nanoparticle Doped YBCO Films Prepared by Chemical Solution Deposition Method," *6th Nanoscience and Nanotechnology Conference*, Izmir, Turkey: 1 page.

Büchel, R. et al. (2009). "Influence of Pt Location on $BaCO_3$ or $Al_2O_3$ During $NO_x$ Storage Reduction," *Journal of Catalysis* 261: 201-207.

(56) References Cited

OTHER PUBLICATIONS

Cospheric LLC. (Mar. 13, 2010). "Porous Ceramics: Application for Polyethylene Microspheres," Microspheres Online, located at http://microspheres.us/microsphere-manufacturing/porous-ceramics-polyethylene-microspheres/177.html, last accessed Mar. 17, 2015, 6 pages.

Strobel, R. et al. (2003). "Flame-made Platinum/Alumina: Structural Properties and Catalytic Behaviour in Enantioselective Hydrogenation," *Journal of Catalysis* 213: 296-304.

Date, A. R. et al. (1987). "The Potential of Fire Assay and Inductively Coupled Plasama Source Mass Spectrometry for the Determination of Platinum Group Elements in Geological Materials," *Analyst* 112: 1217-1222.

Lamouroux, E. et al. (2007). "Identification of Key Parameters for the Selective Growth of Single or Double Wall Carbon Nanotubes on FeMo/$Al_2O_3$ CVD Catalysts," *Applied Catalysts A: General* 323: 162-173.

Martinez-Hansen, V. et al. (2009). "Development of Aligned Carbon Nanotubes Layers Over Stainless Steel Mesh Monoliths," *Catalysis Today* 1475: 571-575.

Panchula, M. L. et al. (2003). "Nanocrystalline Aluminum Nitride: I, Vapor-Phase Synthesis in a Forced-Flow Reactor," *Journal of the American Ceramic Society* 86(7): 1114-1120.

\* cited by examiner

METHOD AND APPARATUS FOR MAKING UNIFORM AND ULTRASMALL NANOPARTICLES

CROSS-REFERENCE TO RELATED APPLICATIONS

The present application is a division of U.S. patent application Ser. No. 12/152,096, filed May 9, 2008 which claims priority to U.S. Provisional Application Ser. No. 60/928,946, filed May 11, 2007, entitled 'MATERIAL PRODUCTION SYSTEM AND METHOD," all of which are hereby incorporated by reference in their entirety as if set forth herein. The co-pending U.S. patent application Ser. No. 11/110,341, filed on Apr. 10, 2005, entitled "HIGH THROUGHPUT DISCOVERY OF MATERIALS THROUGH VAPOR PHASE SYNTHESIS" is incorporated by reference herein in its entirety.

FIELD OF THE INVENTION

The present invention relates to methods of and apparatus for quenching a reactive medium containing gas or vapor phase in order to produce uniform and ultrasmall nanoparticles.

BACKGROUND OF THE INVENTION

Gas or vapor phase particle production is an important technique for producing engineered nanoparticles. In a particle-producing reactor, basic product species are formed within extremely short time spans following ejection of a hot, reactive medium from an energy delivery zone. Following ejection from the delivery zone, further formation mechanisms determine the ultimate characteristics of the final product.

Although chemical reactions such as nucleation and surface growth within precursor materials occur largely during energy delivery, these formation mechanisms continue to be active in the first short moments following ejection. More prevalent in the post-ejection time period are bulk formation mechanisms such as coagulation and coalescence, which operate on already formed particles. Any proper conditioning of the hot, reactive medium following ejection from the energy delivery zone must account for these and other formation mechanisms to form a final product having desired characteristics. In some instances, maintaining a mixture at too high a temperature can lead to overly agglomerated particles in the final product.

In addition to particle formation, proper conditioning must account for post-formation processing of the product. Although particles, once formed, cool rapidly through radiative heat loss, the residual gas in which they are entrained after formation cools much more slowly, and especially so when confined. Confinement is necessary to some degree in any controlled-environment processing system, and economic concerns usually dictate relatively small, confining controlled environments. Therefore, such systems must provide efficient mechanisms for cooling of the entire gas-particle product, yet also provide for efficient transport of the product to collection points within the system.

Transport of particles within a gas stream relies on the entrainment of the particles, which is largely a function of particle properties, e.g., mass, temperature, density, and interparticle reactivity, as well as gas properties, e.g., density, velocity, temperature, density, viscosity, and composite properties, such as particle-gas reactivity. Cooling of a gas by definition affects gas temperature, but also may easily lead to changes in other properties listed above, exclusive of mass.

What is needed in the art is a method of and an apparatus for balancing efficient cooling and transport of a gas-particle product, which requires careful optimization of process parameters.

SUMMARY OF THE INVENTION

In the embodiments of the present invention, features and methods are included to ensure extremely rapid quenching of reactive mixtures from vapor phase to solid phase, thereby producing uniform nanoparticles.

In one aspect of the present invention, a particle production system is provided. The system comprises a plasma production chamber configured to produce a plasma stream. A reaction chamber is fluidly coupled to the plasma production chamber and has an ejection port. The reaction chamber is configured to receive the plasma stream from the plasma production chamber, vaporize a precursor material with the plasma stream to form a reactive mixture stream comprising the vaporized precursor material entrained within plasma stream, and supply the reactive mixture stream to the ejection port. The system also comprises a quench chamber having a wide end, a narrow end, a frusto-conical surface that narrows as it extends from the wide end to the narrow end away from the ejection port of the reaction chamber, a cooled mixture outlet formed at the narrow end, and a quench region formed within the quench chamber between the ejection port and the cooled mixture outlet. The quench region is fluidly coupled to the ejection port of the reaction chamber and is configured to receive the reactive mixture stream from the ejection port of the reaction chamber, to cool the reactive mixture stream to form a cooled mixture stream, and to supply the cooled mixture stream to the cooled mixture outlet. A conditioning fluid injection ring is disposed at the ejection port of the reaction chamber and configured to flow a conditioning fluid directly into the reactive mixture stream as the reactive mixture stream flows through the ejection port of the reaction chamber, thereby disturbing the flow of the reactive mixture stream, creating turbulence within the quench region and cooling the reactive mixture stream to form a cooled mixture stream comprising condensed nanoparticles.

In another aspect of the present invention, a method of producing uniform particles is provided. The method comprises producing a plasma stream within a plasma production chamber, applying the plasma stream to a precursor material, and vaporizing the precursor material with the plasma stream within a reaction chamber, thereby forming a reactive mixture stream comprising the vaporized precursor material entrained within the plasma stream. The reaction chamber is fluidly coupled to the plasma production chamber and has an ejection port. The reactive mixture stream flows through the ejection port and into a quench region of a quench chamber. The quench chamber has a wide end, a narrow end, a frusto-conical surface that narrows as it extends from the wide end to the narrow end away from the ejection port of the reaction chamber, a cooled mixture outlet formed at the narrow end, and the quench region formed within the quench chamber between the ejection port and the cooled mixture outlet. A conditioning fluid flows through an injection ring disposed at the ejection port of the reaction chamber. The conditioning fluid flows directly into the reactive mixture stream as the reactive mixture stream flows through the ejection port of the reaction chamber, thereby disturbing the flow of the reactive mixture stream and creating turbulence within the quench region. The reactive mixture stream is quenched within the quench region to form a cooled mixture stream comprising condensed nanoparticles. The cooled mixture stream flows through the cooled mixture outlet of the quench chamber.

In preferred embodiments, the quench chamber further comprises an annular supply portion disposed between the perimeter of the reaction chamber and the frusto-conical surface. The annular supply portion supplies a conditioning fluid into the quench region in an annular formation along a path different from the flow of the conditioning fluid through the conditioning fluid injection ring. In some embodiments, the annular supply portion comprises a plurality of supply ports disposed in an annular formation around the reaction chamber. In other embodiments, the annular supply portion comprises one continuous supply port disposed in an annular formation around the reaction chamber.

In preferred embodiments, the conditioning fluid injection ring flows the conditioning fluid directly into the reactive mixture stream at an angle substantially perpendicular to the flow of the reactive mixture stream.

In some embodiments the conditioning fluid is a gas. In some embodiments, the conditioning fluid is super-cooled gas or liquid gas, including, but not limited to, liquid nitrogen and liquid helium. The type and form of the conditioning fluid flowing through the injection ring can be the same or different from the conditioning fluid flowing through the annular supply portion.

It is contemplated that the plasma stream can be produced in a variety of ways. However, in a preferred embodiment, the plasma production chamber produces the plasma stream by energizing a working gas.

In some embodiments, the precursor material flows directly into the plasma production chamber via a precursor supply port on the plasma production chamber prior to its vaporization. Additionally or alternatively, the precursor material can flow directly into the reaction chamber via a precursor supply port on the reaction chamber prior to its vaporization.

In preferred embodiments, the reaction chamber comprises an insulating material, thereby forming a enthalpy maintenance region within the reaction chamber. In this respect, the enthalpy of the reactive mixture stream can be maintained at a predetermined threshold level for a period of time within the enthalpy maintenance region of the reaction chamber. Preferably, the reaction chamber comprises a ceramic material.

In preferred embodiments, a collection device is fluidly coupled to the cooled mixture outlet of the quench chamber via a conduit. The conduit preferably has substantially the same diameter as the cooled mixture outlet. The collection device receives the cooled mixture stream from the quench region and separates condensed particles from the cooled mixture stream. Ideally, these condensed particles are nanoparticles.

DETAILED DESCRIPTION OF THE INVENTION

Figure 1:
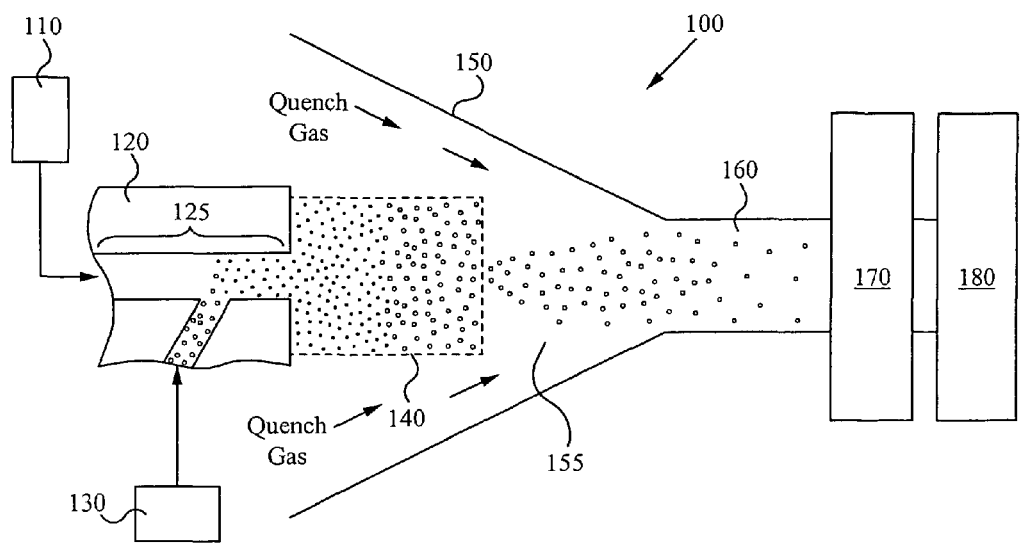
FIG. 1 is a schematic illustration of one embodiment of a system for producing uniform nanoparticles using a quench chamber in accordance with the principles of the present invention.

The description below concerns several embodiments of the invention. The discussion references the illustrated preferred embodiment. However, the scope of the present invention is not limited to either the illustrated embodiment, nor is it limited to those discussed. To the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles. Powders that fall within the scope of the present invention may include, but are not limited to, any of the following: (a) nano-structured powders (nano-powders), having an average grain size less than 250 nanometers and an aspect ratio between one and one million; (b) submicron powders, having an average grain size less than 1 micron and an aspect ratio between one and one million; (c) ultra-fine powders, having an average grain size less than 100 microns and an aspect ratio between one and one million; and (d) fine powders, having an average grain size less than 500 microns and an aspect ratio between one and one million.

The present invention will be readily understood by the following detailed description in conjunction with the accompanying drawings. To facilitate this description, like reference numerals designate like elements.

Preferably, the dimensions of the quench chamber of the present invention have the following general relationships: the diameter of the wide end is substantially greater than that of the ejection port of the reaction chamber, the diameters of the one or more conditioning fluid supply ports are substantially smaller than that of the injection port, the diameter of the narrow end of the constricting chamber is substantially smaller than the diameter of the wide end and substantially equal to the diameter of the ejection port. Additionally, because of the inclusion of the annulus of smaller ports, the diameter of the ejection port is necessarily smaller than that of the wide end of the quench chamber. More specifically, the constricting chamber preferably has a first dimension of approximately 12 inches, constricting to a second dimension of approximately two inches over a distance of 24 inches. Preferred aspect ratios, i.e., ratios of the first diameter to the distance between the first and second ends, range between one to three and one to two.

Flow of the conditioning fluid into the one or more supply ports is preferably caused by formation of a negative pressure differential with the cooled mixture outlet, which also aids in maintaining flow of the mixture through the chamber. This negative pressure differential is preferably formed by fluidly coupling a suction generator or vacuum formation system with the cooled mixture outlet. In alternative embodiments, active injection of conditioning fluid is contemplated, but this scheme has many disadvantages when compared to passively drawing conditioning fluid into the system by vacuum.

Because the present invention preferably uses a pressure differential to motivate flow of the conditioning fluid through the one or more supply ports, variation of the combined surface area of the one or more supply ports allows variation of the flow rate of conditioning fluid. As described below, in some configurations a difference in flow rates between the conditioning fluid sheath and the reactive gas vapor contributes to a conditioning effect of the fluid. Therefore, adjustment of the flow rate of the conditioning fluid permits optimization of the conditioning effect that a flow rate differential provides.

Within the present invention, many configurations of the smoothly varying constrictions of the chamber are contemplated. In the preferred embodiments, these constrictions will smoothly vary in such a way so as to accelerate fluid flow and provide a Venturi-effect pressure differential within the quench chamber. In general, the constriction shape is determined while accounting for several factors affecting the conditioning of the reactive gas-vapor. Two factors are of major concern. First, adequate space must be provided within the region proximal to the first end of the constricting chamber to accommodate rapid expansion of the hot gas-vapor following its flowing into the chamber. Second, constriction of the chamber within the region proximal to the narrow end of the constricting chamber must not occur so rapidly that undue turbulence is introduced into the gas-vapor as it flows to the cooled mixture outlet. For any chamber having fixed length between the wide and narrow ends, these requirements present contradictory design concerns. However, the several embodiments of the present invention include designs that accommodate both concerns.

In a preferred configuration for constrictions within the quench chamber, a cone like (frusto-conical) surface constricts, at a constant rate or otherwise, from the wide end to the cooled mixture outlet at the narrow end. The quench chamber of the present invention preferably comprises a thin shell. The exterior of the quench chamber is can be cooled by a fluid cooling system, to dissipate heat absorbed into the body of the quench chamber from the gas particle mixture. As mentioned above, this heat will primarily be supplied to the quench chamber body in the form of radiation from the newly formed particles as the rapidly cool within the quench chamber. In order to avoid overheating of the chamber body, the fluid cooling system is preferably included.

The present invention considers a wide variety of gas phase particle production systems including combustion-based systems, plasma based systems, laser ablation systems and vapor deposition systems. The preferred systems take material inputs in a broad range of forms, including solid phase inputs, and provide product in high surface area forms, including nanopowders. In addition, the process controls preferably provide a fine degree over a plurality of reaction parameters, permitting fine gradients of product composition ratios to be produced.

A wide variety of material types and forms can be processed in preferable particle production reactors used in the present invention. Without prejudice, the present invention specifically considers the provision of materials in the following forms: solid, liquid and gas. An exemplary particle production system is a plasma powder production reactor, which is included within several of the exemplary embodiments discussed below. The plasma reactors considered within the present invention can have many means of energy delivery, including the following: DC coupling, capacitive coupling, inductive coupling, and resonant coupling. In general, vapor phase nanopowder production means are preferred. The embodiments of the present invention can use elements of nano-powder production systems similar to those disclosed in U.S. patent application Ser. No. 11/110,341, filed on Apr. 19, 2005 and entitled, "HIGH THROUGHPUT DISCOVERY OF MATERIALS THROUGH VAPOR PHASE SYNTHESIS", which is currently published as U.S. Publication No. 2005-0233380-A. In such a nano-powder production system, working gas is supplied from a gas source to a plasma reactor. Within the plasma reactor, energy is delivered to the working gas, thereby creating a plasma. A variety of different means can be employed to deliver this energy, including, but not limited to, DC coupling, capacitive coupling, inductive coupling, and resonant coupling. One or more material dispensing devices introduce at least one material, preferably in powder form, into the plasma reactor. The combination within the plasma reactor of the plasma and the material(s) introduced by the material dispensing device(s) forms a highly reactive and energetic mixture, wherein the powder can be vaporized. This mixture of vaporized powder moves through the plasma reactor in the flow direction of the working gas.

Referring now to FIG. 1, the particle production system 100 comprises a plasma production unit 120 having plasma production chamber 125. The plasma production chamber 125 is preferably disposed within the plasma production unit 120, which can include several types of inputs for power, gas, and precursor materials. Inputs are provided to the plasma production chamber 125 by a variety of supply systems.

The plasma production unit 120 is configured to produce a plasma stream within the plasma production chamber 125. It is contemplated that the plasma stream can be produced in a variety of ways. However, in a preferred embodiment, a working gas flows from a working gas supply device 110 into the plasma production chamber 125, where energy is delivered to it, thereby forming the plasma stream. Preferably, an overall system controller provides control signals to the working gas supply device 110. Additionally, a power supply system (not shown) can also be coupled to the plasma production chamber 125. Preferably, the overall system controller provides control signals to the power supply system as well.

A reaction chamber 140 is fluidly coupled to the plasma production chamber 125 and configured to receive the plasma stream from the plasma production chamber 125. In a preferred embodiment, the reaction chamber 140 has a larger diameter than the plasma production chamber 125.

In some embodiments, the plasma production chamber 125 is fluidly coupled with a material supply device 130, thereby allowing precursor material, such as powder, from the material supply device 130 to be delivered directly into the plasma production chamber 125. Precursor material is stored within the material supply 130. A material supply conduit preferably passes from the material supply device 130 to the plasma production chamber 125. The material supply device 130 preferably includes a controllable delivery system that provides material to the conduit. Preferably, the conduit enters though airtight seals and terminates within the plasma production unit 120 at a selected location. Furthermore, an overall system controller is preferably configured to supply control signals to the material supply device 130. Additionally or alternatively, the material supply device 130 can be fluidly coupled directly to the reaction chamber 140, thereby allowing precursor material from the material supply device 130 to be delivered directly into the reaction chamber 140.

In embodiments where the precursor material is delivered into the plasma production chamber 125, the plasma stream mixes with the precursor material, forming a reactive mixture stream. The coupling between the plasma production chamber 125 and the reaction chamber 140 permits delivery of the mixture stream from the plasma production unit 120 into the reaction chamber 140.

In some embodiments, portions of the reaction chamber 140 are constructed of an insulating material configured to maintain the enthalpy of a plasma stream within a portion thereof above a predetermined threshold. Preferably, maintaining the enthalpy of the plasma extends a resonance time of the plasma within the reaction chamber 140. In some embodiments, portions of the reaction chamber 140 are constructed of a material with high thermal durability. In these embodiments, the portions so constructed are configured to attain a high temperature during operation of the reaction chamber 140. In some embodiments, portions of the reaction chamber 140 are constructed of a ceramic material. Preferably, the material used is boron nitride.

Within the reaction chamber 140, the plasma stream preferably vaporizes the precursor material, thereby forming a reactive mixture stream comprising the vaporized precursor material entrained within the plasma stream. In some embodiments, this vaporization of precursor material can begin in the plasma production chamber 125 if the precursor material is introduced into the plasma production chamber 125.

Preferably, reaction chamber 140 is shaped and the operational parameters of the system 100 are controlled so that as the mixture stream enters the reaction chamber 140, it is maintained above an enthalpy threshold. This maintenance takes place within an enthalpy maintenance region somewhere within the reaction chamber 140. Preferably, the average enthalpy of the mixture stream falls as it moves away from the enthalpy maintenance region with its minimum enthalpy (within the reaction chamber 140) coming at the ejection port to the quench region 155. In some embodiments, the resonance time of the mixture within the chamber 140 is above a threshold length of time controlled by an overall system controller.

Furthermore, in some embodiments of the present invention, the reaction chamber 140 is constructed and the operational parameters of the apparatus 100 are chosen so that the vaporized precursor material begins to condense within the mixture stream while it is within the reaction chamber 140. In some other embodiments, construction and operational parameters of the system 100 are chosen so that the vaporized precursor material begins to condense within the mixture stream while it is within the quench region 155.

A quench chamber 150 is fluidly coupled to the reaction chamber 140 through an ejection port at the end of the reaction chamber 140. The ejection port is configured to supply the reactive mixture stream from the reaction chamber 140 into a quench region 155 of the quench chamber 150. In a preferred embodiment, the reaction chamber 150 has a frusto-conical shape, narrowing as it extends away from the ejection port and towards a cooled mixture outlet. Although the figures show quench chamber 150 substantially open at the wide end, preferably the wide end of the quench chamber 150 is substantially closed except for fluid ports through which a fluid can be received. The cooled mixture outlet is disposed at the narrow end of the quench chamber 150 that preferably leads into a cooling conduit 160. The quench region 155 is formed within the quench chamber 150 between the ejection port of the reaction chamber 140 and the cooled mixture outlet. In a preferred embodiment, an annular supply portion is formed between the perimeter of the reaction chamber 140 and the quench chamber 150. This annular supply portion can comprise a plurality of supply inlets or one continuous supply inlet disposed in an annular formation around the ejection port of the reaction chamber 140. The annular supply portion is configured to supply a conditioning fluid, preferably from a conditioning fluid supply device, to the quench region 155. In a preferred embodiment, these supply inlets are channels of adjustable size that directly couple the conditioning fluid supply to the quench region 155, yet permit for controlled flow of the conditioning fluid to the quench region 155. In FIG. 1, conditioning gas is supplied roughly along the vectors marked "Quench Gas." In a preferred embodiment, the conditioning fluid is supplied through airtight inlets and outlets to the quench region 155 (preferably from a dedicated supply of conditioning fluid), where it preferably mixes with and cools the reactive mixture stream from the reaction chamber 140.

Motive fluid flow within the system can be motivated by a suction generator 180, such as a motive vacuum pump, pulling a negative pressure on a cooling conduit 160 that is fluidly coupled to the cooled mixture outlet of the quench chamber 150, thereby motivating mass flow through the outlet of the quench region 155. However, the flow rate of the motive fluid into the quench region 155 is preferably controlled by the overall control system.

The cooling conduit 160 receives the particle and gas mixture from the quench region 155. Preferably, the mixture is pulled into the cooling conduit 160 by the suction generator 180. However, in some embodiments, a motive pump or other system within a sampling or collection device 170 provides some motive force to pull the mixture. Of course, to some extent, pressure provided by the plasma production chamber 125 and the conditioning fluid supply can motivate the flow of the mixture into the cooling conduit 160.

In some embodiments, the cooling conduit 160 is equipped with an active cooling system. In some embodiments, a conditioning fluid, such as argon, is supplied into the gas input couplings of the cooling conduit 160. In some of these embodiments, the conditioning fluid is a cooling and entraining gas. In some of these embodiments, the conditioning fluid is a passivating gas.

The cooling conduit 160 fluidly connects the quench region 155 with a sampling or collection device 170. The conduit 160 is preferably coupled to the quench region 155 through airtight means. The collection device 170 is preferably positioned between the cooling conduit 160 and the suction generator 180. The collection device 170 is configured to receive the cooled mixture via the cooling conduit 160, sample or collect material, such as condensed particles, having appropriate characteristics from the mixture, and permit remains of the mixture to flow to the suction generator 180, which is fluidly coupled through a conduit. Furthermore, the collection device 170 can take multiple samples, at selected times, and can sample discontinuously, which allows for sampling from a gas-particle streams whose composition may vary from time to time without contamination from previous product.

It is contemplated that the collection device 170 can be configured in a variety of ways. In one embodiment, the collection device 170 comprises a sampling structure, at least one filled aperture formed in the sampling structure, and at least one unfilled aperture formed in the sampling structure. Each filled aperture is configured to collect particles from the mixture stream, such as by using a filter. The sampling structure is configured to be adjusted between a pass-through configuration and a collection configuration. The pass-through configuration comprises an unfilled aperture being fluidly aligned with a conduit, such as the cooling conduit 280, thereby allowing the unfilled aperture to receive the mixture stream from the conduit and the mixture stream to flow through the sampling structure without substantially altering the particle content of the mixture stream. The collection configuration comprises a filled aperture being fluidly aligned with the conduit, thereby allowing the filled aperture to receive the mixture stream and collect particles while the mixture stream is being flown through the filled aperture.

It is contemplated that the sampling structure can be adjusted between the pass-through configuration and the collection configuration in a variety of ways. In one embodiment, the sampling structure is a disk-shaped structure including an annular array of apertures, wherein the annular array comprises a plurality of the filled apertures and a plurality of the unfilled apertures. The sampling structure is rotatably mounted to a base, wherein rotational movement of the sampling structure results in the adjustment of the sampling structure between the pass-through configuration and the collection configuration. In another embodiment, the sampling structure is a rectangular-shaped structure including a linear array of apertures, wherein the linear array comprises a plurality of the filled apertures and a plurality of the unfilled apertures. The sampling structure is slideably mounted to a base, wherein sliding of the sampling structure results in the adjustment of the sampling structure between the pass-through configuration and the collection configuration.

As mentioned above, the collection device 170 preferably permits the suction generator 180 to provide a motive force therethrough. However, in some embodiments, the collection device 170 provides additional motive force. In some embodiments, a collection device 170 supplants the motive force provided by the suction generator 180 and provides a substitute motive force to the cooling conduit 160.

The overall control system (not shown) sends signals to the working gas supply 110 and power supply to set operational parameters. Parameters for the working gas supply 110 determine the rate at which the working gas feeds into the plasma production chamber 125. Power supply parameters determine the voltage and amperage at which power is supplied to the plasma production chamber 125. In combination, these parameters determine the characteristics of the plasma produced within the plasma production chamber 125. Furthermore, the material supply device 130 provides a metered stream of material through the material supply conduit to the conduit's terminus location within the plasma production chamber 125. This exposes the material to plasma within the chamber. The rate at which material is provided into the chamber 125 preferably is determined by the overall control system. This rate, and other system parameters, determines characteristics of the mixture stream formed within the plasma production chamber 125. Furthermore, although the material supply device 130 is described as providing only a single material into the plasma production chamber 125 at a single location, in some embodiments of the present invention, the material supply device 130 supplies a plurality of materials into the plasma production chamber 125 and/or the reaction chamber 140 at one or more locations.

In the system 100, the mass flow rate of material through the system is controlled to permit effective quenching at achievable conditioning fluid flow rates. Preferably, this rate is controlled via the mass flow rate of material into the plasma production chamber 125. Specifically, the material supply device 130 and the control system are configured to control a mass flow rate delivery of the precursor material into the plasma stream to achieve a rate that permits cooling of the mixture stream to one quarter of the melting point of the material extremely rapidly. Preferably, this flow rate is selected with reference to achievable conditioning fluid flow rates within the quench region 155 and with reference to achievable turbulence within the quench region 155.

Figure 3:
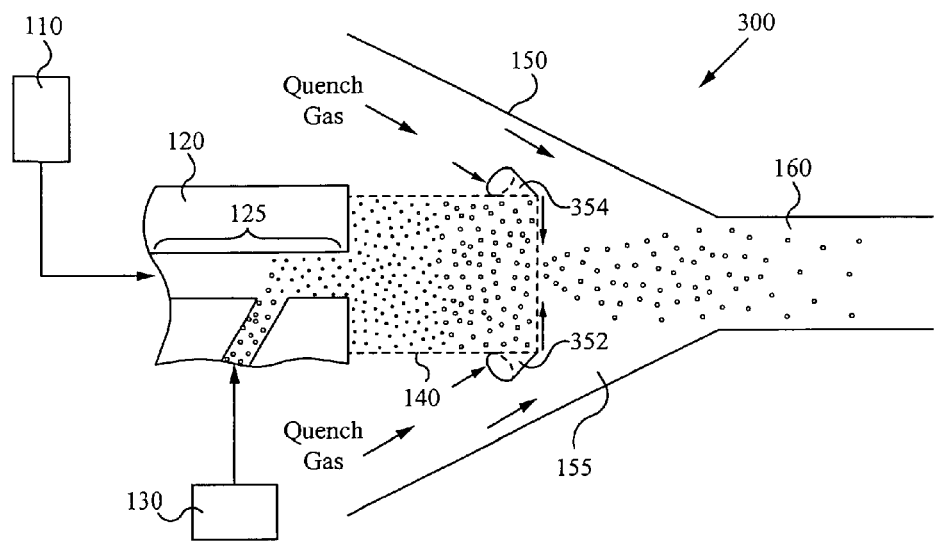
FIG. 3 is a schematic illustration of one embodiment of a system for producing uniform nanoparticles using a quench gas in a turbulent quench chamber in accordance with principles of the present invention.
Figure 4:
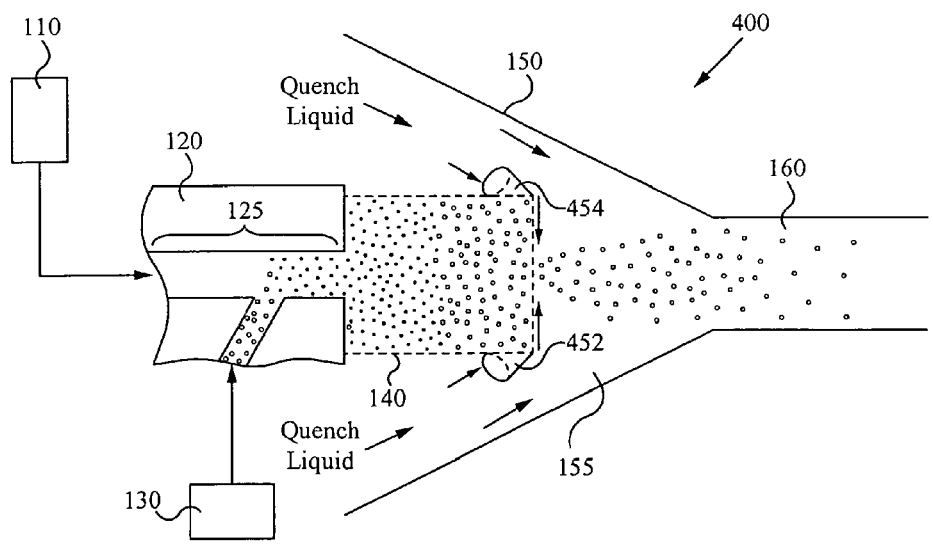
FIG. 4 is a schematic illustration of one embodiment of a system for producing uniform nanoparticles using a liquid conditioning fluid in a turbulent quench chamber in accordance with the principles of the present invention.

While the configuration of system 100 provides an improvement in terms of quench rate over the prior art, the quench rate can be further improved. FIGS. 3 and 4 illustrate systems similar to system 100, but with additional features that result in an improved quench rate.

FIG. 3 illustrates one embodiment of a particle production system 300. In the system 300, the reactive mixture flows from the reactor chamber 140 into the quench region 155, such as in FIG. 1. While the mixture flows into the quench region 155, conditioning fluid, labeled "Quench Gas" is supplied into the quench region 155 via an annular supply portion similar to the annular supply portion discussed above. A portion of the conditioning fluid is diverted or other wise supplied to an injection ring disposed at the end of the reaction chamber 140. This injection ring is configured to flow the quench gas directly into the reactive mixture stream as the reactive mixture stream flows through the ejection port of the reaction chamber 140, thereby disturbing the flow of the reactive mixture stream, creating turbulence within the quench region and cooling the reactive mixture stream at the earliest point possible as the mixture leaves the reaction chamber.

It is contemplated that the injection ring can be configured in a variety of ways. In preferred embodiments, the injection ring flows the conditioning fluid directly into the reactive mixture stream at an angle substantially perpendicular to the flow of the reactive mixture stream. However, it is contemplated that other injection angles are within the scope of the present invention as well. Furthermore, in a preferred embodiment, the injection ring comprises a plurality of injection ports, such as nozzle structures 352 and 354, disposed in an annular configuration around flow of the reactive mixture. The injection ring is configured to induce a high degree of turbulence within the conditioning fluid and the reactive mixture, and ultimately the quench region 155.

As the reactive mixture moves out of the reaction chamber 140, it expands and mixes with the conditioning fluid. Parameters related to conditioning fluid supply are controlled to permit the nozzles 352 and 354 to produce a high degree of turbulence and promote mixing with the reactive mixture. This turbulence can depend on many parameters. Preferably, one or more of these parameters are adjustable to control the level of turbulence. These factors include, but are not limited to, the flow rates of the conditioning fluid and any modification to the flow path of the fluid.

After entering the quench region 155, particle formation mechanisms are active. The degree to which the particles agglomerate depends on the rate of cooling. The cooling rate depends on the turbulence of the flow within the quench region. Preferably, the system is adjusted to form a highly turbulent flow, and to form very dispersed particles. For example, in preferred embodiments, the turbidity of the flow within the quench region is such that the flow has a Reynolds Number of at least 1000. Preferably, the turbulence is controlled to achieve a rate of cooling of the mixture stream that moves the mixture stream temperature to one quarter of the melting point of the material within a very short time after the reactive mixture exits the reaction chamber 140.

Following injection into the quench region, cooling, and particle formation, the mixture flows from the quench chamber 150 into the cooling conduit 160. Suction generated by an external device, such as the suction generator previously discussed, preferably moves the cooled mixture from the quench region 155 into the conduit 160. The cooled mixture can flow to a collection or sampling device, such as described above with respect to FIG. 1.

In FIG. 3, the conditioning fluid supplied to the quench region through the injection ring disposed at the ejection port of the reaction chamber 140 and through the annular supply portion disposed between the perimeter of the reaction chamber 140 and the quench chamber 150 is a gas. In one embodiment, the gas supplied is argon. However, other gases can be used as well.

Figure 2:
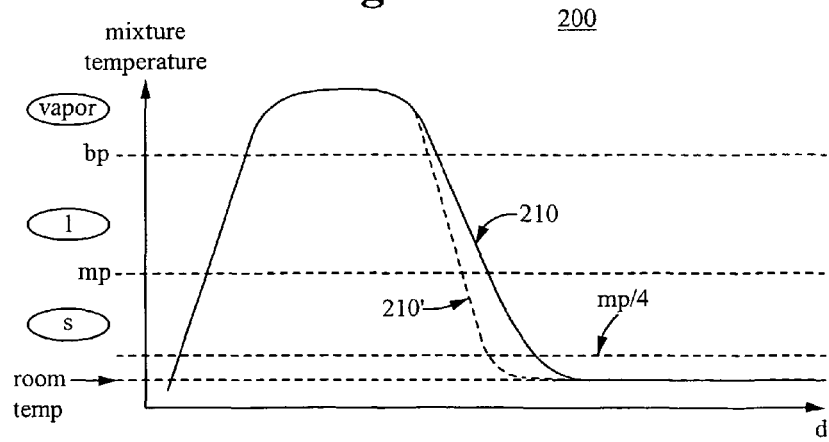
FIG. 2 is a graph illustrating average mixture temperature in relation to time and distance as material is introduced, vaporized and cooled within embodiments of the present invention.

It is contemplated that in addition to a gas being used as the conditioning fluid, a super-cooled gas, or liquid gas, can be used as the conditioning fluid. Such conditioning fluids include, but are not limited to, liquid nitrogen and liquid helium. In FIG. 4, system 400 provides a conditioning fluid to the quench region 155 in the form of a liquid gas, which is labeled as "Quench Liquid." In a preferred embodiment, the quench liquid flows through an injection ring directly into the reactive mixture as the reactive mixture leaves the reaction chamber 140, similar to the quench gas described above with respect to FIG. 3. However, it is contemplated that any combination or configuration of the features illustrated in FIGS. 2-4 are within the scope of the present invention. For example, a quench gas can be supplied through the annular supply portion, while a quench liquid is supplied through the injection ring. Alternatively, the quench liquid can be supplied through the annular supply portion and into the quench region 155 without the use of the injection ring.

Preferably the temperature of the liquid and the flow rate thereof are configured to achieve a rate of cooling of the mixture stream that moves the mixture stream temperature to one quarter of the melting point of the material within an extremely short time after the reactive mixture leaves the reaction chamber 140. The hot reactive mixture absorbs the moisture from the quench liquid, thus resulting in an increased quench rate above that achieved by only using a quench gas. Preferably the temperature and conditioning liquid flow rate are selected with reference to desired mass flow rates within the system.

Figure 5:
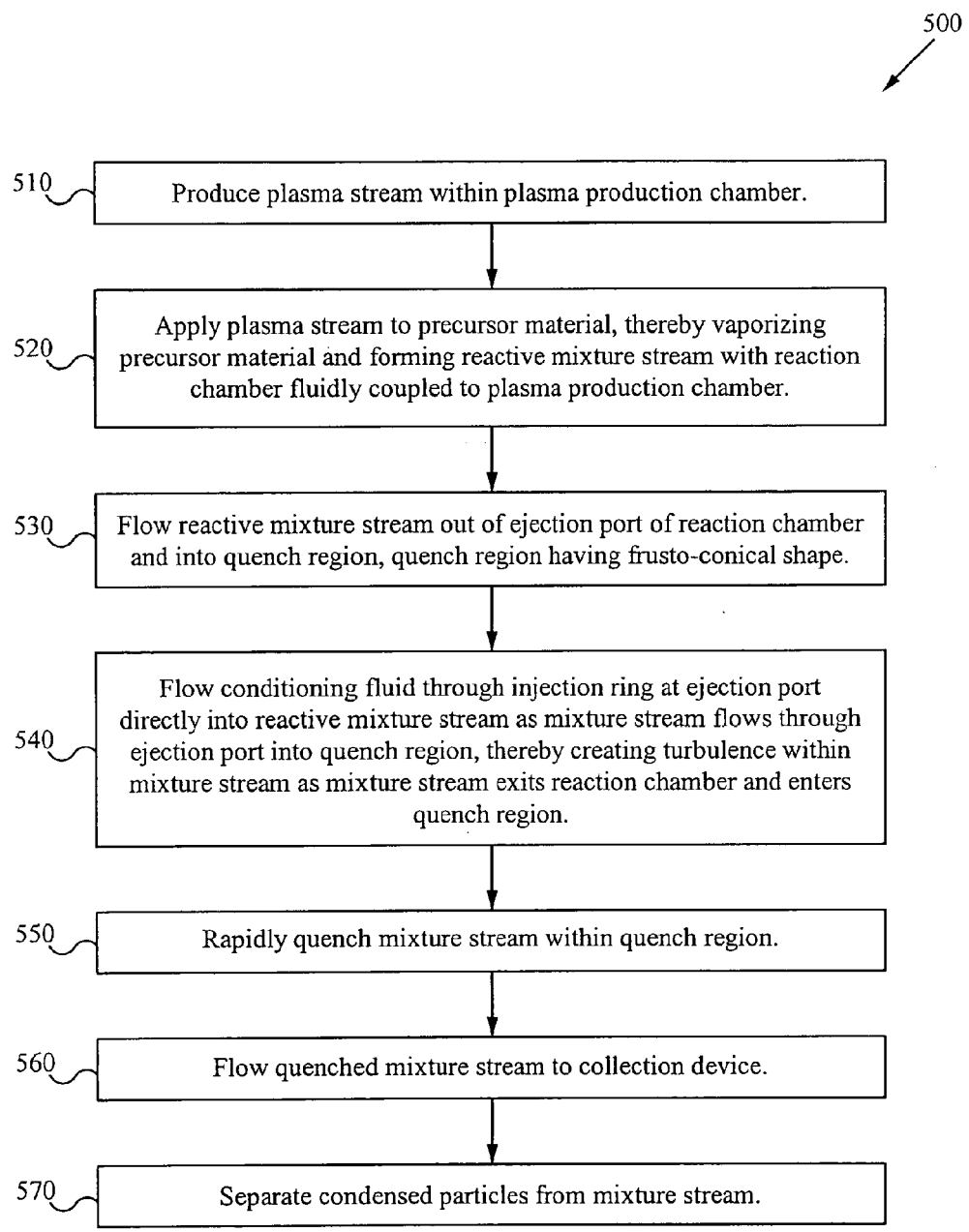
FIG. 5 is a flowchart illustrating one embodiment of a method of producing uniform nanoparticles in accordance with the principles of the present invention.

FIG. 5 is a flowchart illustrating one embodiment of a method 500 of producing uniform nanoparticles in accordance with the principles of the present invention. As would be appreciated by those of ordinary skill in the art, the protocols, processes, and procedures described herein may be repeated continuously or as often as necessary to satisfy the needs described herein. Additionally, although the steps of method 500 are shown in a specific order, certain steps may occur simultaneously or in a different order than is illustrated. Accordingly, the method steps of the present invention should not be limited to any particular order unless either explicitly or implicitly stated in the claims.

At step 510, a plasma stream is produced within a plasma production chamber. It is contemplated that the plasma stream can be produced in a variety of ways. However, in a preferred embodiment, the plasma production chamber produces the plasma stream by energizing a working gas that flows through the chamber.

At step 520, the plasma stream is applied to a precursor material, thereby vaporizing the precursor material. This application of the plasma stream to the precursor material can tale place in the plasma production chamber and/or in a reaction chamber fluidly coupled to the plasma production chamber. Either way, the plasma stream flows into the reaction chamber and a reactive mixture stream is formed within the reaction chamber. The reactive mixture stream preferably comprises the vaporized material entrained within the plasma stream.

At step 530, the reactive mixture stream flows through the ejection port of the reaction chamber and into a quench region of a quench chamber. The quench chamber has a wide end, a narrow end, a frusto-conical surface that narrows as it extends from the wide end to the narrow end away from the ejection port of the reaction chamber, a cooled mixture outlet formed at the narrow end, and the quench region formed within the quench chamber between the ejection port and the cooled mixture outlet.

At step 540, a conditioning fluid flows through an injection ring disposed at the ejection port of the reaction chamber. The conditioning fluid flows directly into the reactive mixture stream as the reactive mixture stream flows through the ejection port of the reaction chamber, thereby disturbing the flow of the reactive mixture stream and creating turbulence within the quench region. As discussed above, the conditioning fluid is preferably a gas or a liquid gas. Additionally, or alternatively, the conditioning fluid can be supplied through the annular supply portion disposed between the perimeter of the reaction chamber and the quench chamber.

At step 550, the reactive mixture stream is rapidly quenched within the quench region to form a cooled mixture stream. The cooled mixture stream preferably comprises condensed nanoparticles.

At step 560, the cooled mixture stream flows through the cooled mixture outlet of the quench chamber to a collection device, preferably via a conduit. In a preferred embodiment, the conduit has substantially the same diameter as the cooled mixture outlet.

At step 570, the collection device separates condensed particles from the cooled mixture stream as the cooled mixture stream flows through the collection device. In a preferred embodiment, the collection device separates the condensed particles from the cooled mixture stream by using one or more filters.

FIG. 2 illustrates a graph 200 showing the intended effect of features of embodiments of the present invention on quench rates in particle production systems. The graph 200 charts exemplary variations in gas/material or mixture temperature with time (position in the apparatus) as they enter a plasma production chamber, such as chamber 125, vaporize or become plasma, mix, travel into a reaction chamber, such as reaction chamber 140, begin to form particles, and enter the quench region, such as quench region 155. Relationships between position within the apparatus and position on the graph are roughly illustrated by vertical correlation between FIGS. 1 and 2.

The vertical axis of the graph charts mixture temperature. The oval legends denote phases of matter for the material being operated on by the apparatus. Vapor is on top, below that liquid, and below that solid. The dashed lines indicate critical temperatures relative to the material concerned. The 'bp' line denotes boiling point, the 'mp' line denoted melting point. The 'mp/4' line denotes one quarter of the material melting point.

Within the plasma production chamber 125, the temperature rapidly increases, causing sublimation of the material from solid phase to vapor phase. As the mixture moves into the reactor chamber, 140 the temperature and enthalpy of the mixture remain substantially constant, staying within the vapor phase of the material. However, as the mixture moves to the end of the reaction chamber 140, the temperature decreases, reaching a minimum (within the reaction chamber) at the downstream edge of the reaction chamber 140.

Once ejected, the mixture enters the quench region 155, where it expands and cools rapidly. One or more of highly turbulent flow, sufficiently low mass flow rate, and liquid quenching with super cooled gas forms sufficient mixing of the mixture with conditioning fluid to cool the mixture smoothly and rapidly through 'bop', liquid phase, 'mp' and part of solid phase to 'mp/4' within a short enough time to avoid undesired agglomeration and promote the production of uniform nanoparticles. The supply of conditioning fluid through the annular supply portion results in the quench rate illustrated as line 210. While this quench rate is a substantial improvement over the prior art, the use of the injection ring and/or the liquid gas results in an even faster quench rate illustrated as line 210'.

During resonance within the reaction chamber and quench region, particles form. Because the mixture is cooled rapidly, there is a short time period during which agglomeration occurs. As the mixture of particles and hot gas continues to mix with the conditioning fluid, the mixture of gas and particles moves out of the narrow end into the conduit. Overall, the quench period within a highly turbulent quench region and/or a quench region fed by a super-cooled gas conditioning liquid as in some embodiments of the present invention is much shorter than with standard quenching. Eventually the conditioning fluid and the mixture reach thermal equilibrium, preferably at room temperature.

Thus, features of the embodiments of the present invention decrease the period during which particles formed can agglomerate with one another. Ultimately, this decrease in potential agglomeration produces particles of more uniform size, and in some instances produces smaller-sized particles. Both of these features lead to particles with increased dispersiblity and increased ratio of surface area to volume.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A method of producing nanoparticles, the method comprising:
   vaporizing a precursor material with a plasma stream within a reaction chamber, thereby forming a reactive mixture stream comprising the vaporized precursor material entrained within the plasma stream;
   flowing the reactive mixture stream through an ejection port of the reaction chamber and into a quench region of a quench chamber having a frusto-conical surface that narrows as it extends away from the ejection port of the reaction chamber, wherein the ejection port is located within a frusto-conical-shaped portion of the quench chamber;
   flowing a conditioning fluid through an injection ring disposed at the ejection port of the reaction chamber into the reactive mixture stream as the reactive mixture stream flows through the ejection port of the reaction chamber, thereby disturbing the flow of the reactive mixture stream and creating turbulence within the quench region;
   quenching the reactive mixture stream within the quench region to form a cooled mixture stream comprising condensed nanoparticles; and
   flowing the cooled mixture stream through a cooled mixture outlet of the quench chamber.

2. The method of claim 1, further comprising supplying the conditioning fluid into the quench region in an annular formation along a path different from the flow of the conditioning fluid through the conditioning fluid injection ring via an annular supply portion formed between the reaction chamber and the frusto-conical surface of the quench chamber.

3. The method of claim 2, wherein the annular supply portion comprises a plurality of supply ports disposed in an annular formation around the reaction chamber.

4. The method of claim 2, wherein the annular supply portion comprises one continuous supply port disposed in an annular formation around the reaction chamber.

5. The method of claim 1, wherein the conditioning fluid injection ring flows the conditioning fluid into the reactive mixture stream at an angle substantially perpendicular to the flow of the reactive mixture stream.

6. The method of claim 1, wherein the conditioning fluid is a super-cooled gas.

7. The method of claim 1, wherein the conditioning fluid is liquid nitrogen.

8. The method of claim 1, wherein the conditioning fluid is liquid helium.

9. The method of claim 1, wherein the plasma stream is produced within a plasma production chamber by energizing a working gas.

10. The method of claim 9, further comprising flowing the precursor material into the plasma production chamber via a precursor supply port on the plasma production chamber prior to its vaporization.

11. The method of claim 1, further comprising flowing the precursor material into the reaction chamber via a precursor supply port on the reaction chamber prior to its vaporization.

12. The method of claim 1, further comprising maintaining the enthalpy of the reactive mixture stream for a period of time within an enthalpy maintenance region within the reaction chamber, wherein the reaction chamber comprises an insulating material.

13. The method of claim 12, wherein the reaction chamber comprises a ceramic material.

14. The method of claim 1, further comprising:
   flowing the cooled mixture stream from the quench region to a collection device via a conduit having substantially the same diameter as the cooled mixture outlet; and
   separating condensed nanoparticles from the cooled mixture stream using the collection device.

15. The method of claim 1, wherein the conditioning fluid is argon.

16. A method of producing nanoparticles comprising:
   applying a plasma stream to a precursor material within a reaction chamber, thereby forming a reactive mixture stream comprising vaporized precursor material entrained within the plasma stream;
   flowing the reactive mixture stream through an ejection port of the reaction chamber and into a frusto-conical-shaped quench chamber, wherein the ejection port is located within the frusto-conical-shaped quench chamber; and
   flowing a conditioning fluid into the reactive mixture stream as the reactive mixture stream flows through the ejection port to disturb the flow of the reactive mixture stream and to cool the reactive mixture stream to form a cooled mixture stream comprising condensed nanoparticles.

17. The method of claim 16, wherein the conditioning fluid flows through an injection ring disposed at the ejection port into the reactive mixture stream at an angle substantially perpendicular to the flow of the reactive mixture stream out through the ejection port.

18. The method of claim 17, wherein the injection ring induces a high degree of turbulence within the conditioning fluid and the reactive mixture stream.

19. The method of claim 17, wherein the injection ring comprises one or more injection ports.

20. The method of claim 16, wherein the plasma stream is produced within a plasma production chamber.

21. The method of claim 20, further comprising supplying the precursor material into the plasma production chamber prior to its vaporization.

22. The method of claim 16, further comprising supplying the precursor material into the reaction chamber prior to its vaporization.

* * * * *